(12) United States Patent
Fontayne

(10) Patent No.: US 6,629,960 B2
(45) Date of Patent: Oct. 7, 2003

(54) NEEDLE HUB FOR MEDICAL INSTRUMENT

(75) Inventor: Diego Fontayne, Montebello, NY (US)

(73) Assignee: Integrated Implant Systems, LL.C., Arlington, VA (US)

( * ) Notice: Subject to any disclaimer, the term of this patent is extended or adjusted under 35 U.S.C. 154(b) by 307 days.

(21) Appl. No.: 09/858,603

(22) Filed: May 17, 2001

(65) Prior Publication Data

US 2002/0007151 A1 Jan. 17, 2002

Related U.S. Application Data

(60) Provisional application No. 60/281,825, filed on Apr. 6, 2001, and provisional application No. 60/205,053, filed on May 18, 2000.

(51) Int. Cl.[7] ............................. A61M 5/00; A61M 5/31
(52) U.S. Cl. ...................................... 604/240; 604/61
(58) Field of Search ................................ 600/8, 7, 459, 600/1, 439; 128/1.2; 604/61, 240; 606/96, 439

(56) References Cited

U.S. PATENT DOCUMENTS

| | | |
|---|---|---|
| 3,704,707 A | 12/1972 | Halloran |
| 4,267,149 A | 5/1981 | Bruckner et al. |
| 4,400,170 A | 8/1983 | McNaughton et al. |
| 4,451,254 A | 5/1984 | Dinius et al. |
| 4,490,142 A | 12/1984 | Silvern ....................... 604/241 |
| 4,700,692 A | 10/1987 | Baumgartner |
| 4,838,265 A | 6/1989 | Cosman et al. |
| 5,242,373 A | 9/1993 | Scott et al. |
| 5,305,203 A | 4/1994 | Raab |
| 5,366,896 A | 11/1994 | Margrey et al. |
| 5,514,101 A | 5/1996 | Schulz et al. |
| 5,609,152 A | 3/1997 | Pellegrino |
| 5,616,136 A | 4/1997 | Shillington et al. ......... 604/240 |
| 5,860,909 A | 1/1999 | Mick et al. |
| 5,871,448 A | 2/1999 | Ellard |
| 5,876,379 A | 3/1999 | Beauvais et al. ........... 604/181 |
| 5,919,169 A | 7/1999 | Grams et al. ................ 604/241 |
| 6,002,859 A | 12/1999 | DiGioia, III et al. |
| 6,007,474 A | 12/1999 | Rydell |
| 6,102,844 A | 8/2000 | Ravins et al. |
| 6,129,670 A | 10/2000 | Burdette et al. |
| 6,132,358 A | 10/2000 | Glenn et al. |
| 6,206,832 B1 | 3/2001 | Downey et al. |
| 6,214,013 B1 | 4/2001 | Lambrecht et al. |
| 6,267,718 B1 | 7/2001 | Vitali et al. |
| 6,270,472 B1 | 8/2001 | Antaki et al. |
| 6,387,034 B1 | 5/2002 | Lee |
| 6,432,035 B1 | 8/2002 | Ravins et al. |

FOREIGN PATENT DOCUMENTS

| | | |
|---|---|---|
| FR | 2733916 | 11/1996 |
| WO | WO 97/22379 | 6/1997 |

*Primary Examiner*—Henry Bennett
*Assistant Examiner*—Sabrina Dagostino
(74) *Attorney, Agent, or Firm*—Heller Ehrman White and McAuliffe

(57) ABSTRACT

A medical instrument includes a needle nozzle that accepts a needle cam. A needle hub assembly includes a needle hub and a needle cannula, and when registration ribs of the needle hub are fitted between respective registration ribs of the needle cam, the needle is thereby fitted onto the medical instrument.

5 Claims, 24 Drawing Sheets

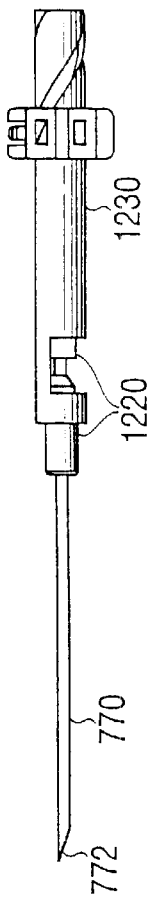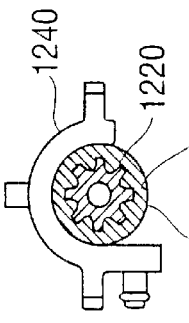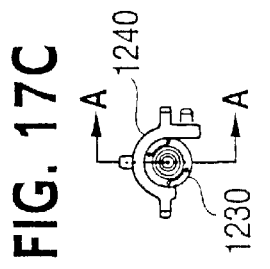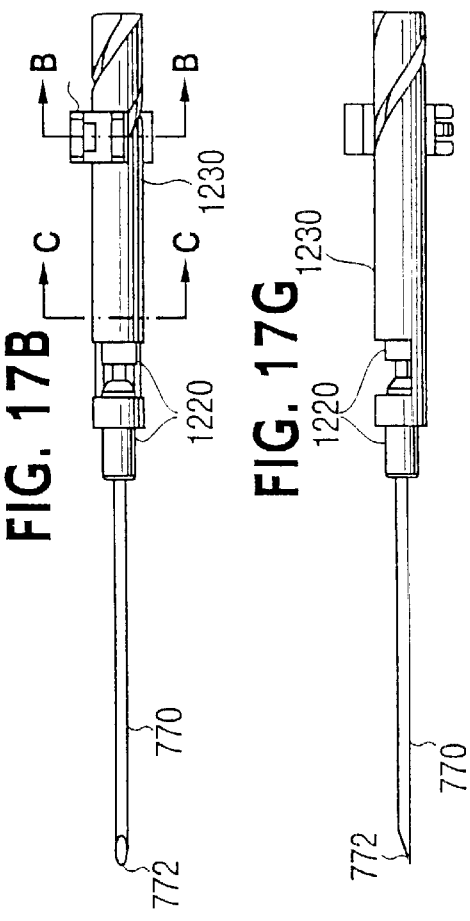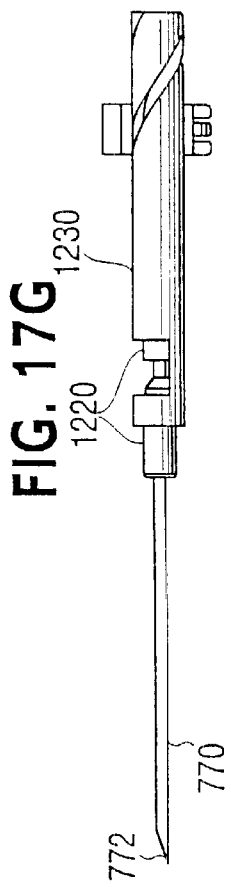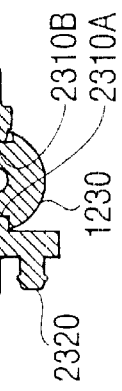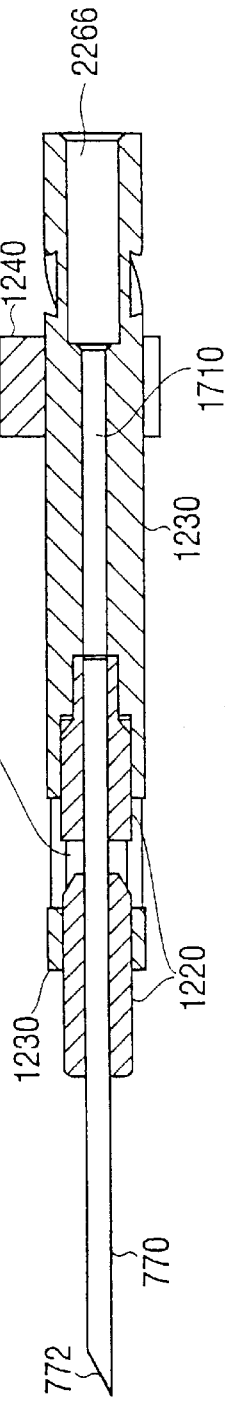

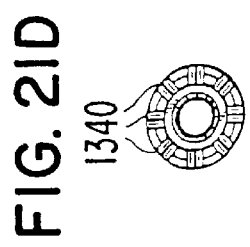
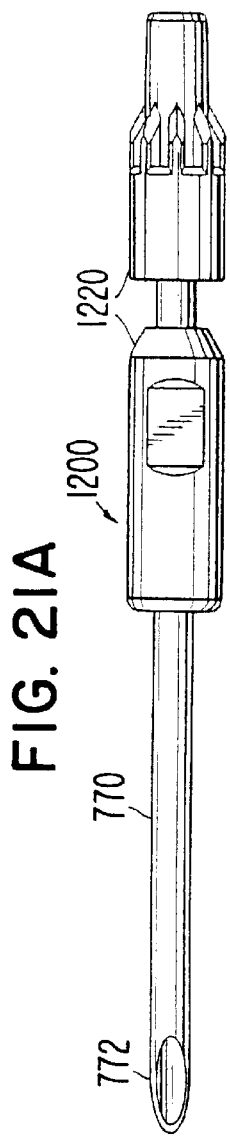
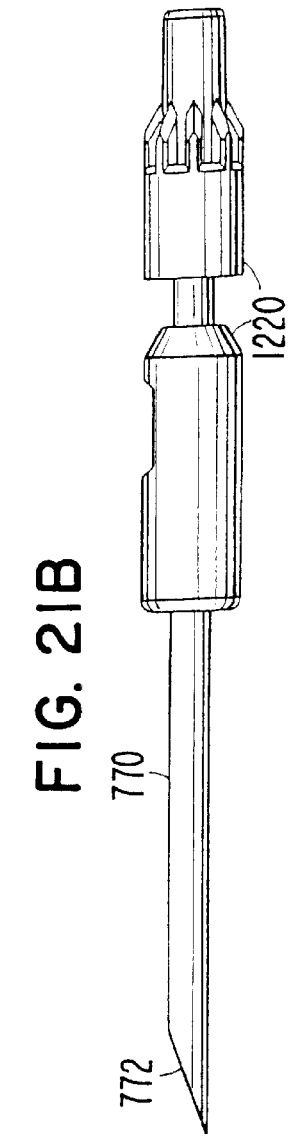
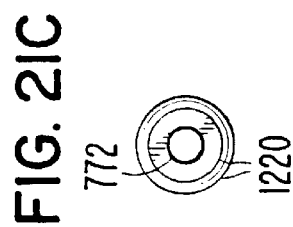
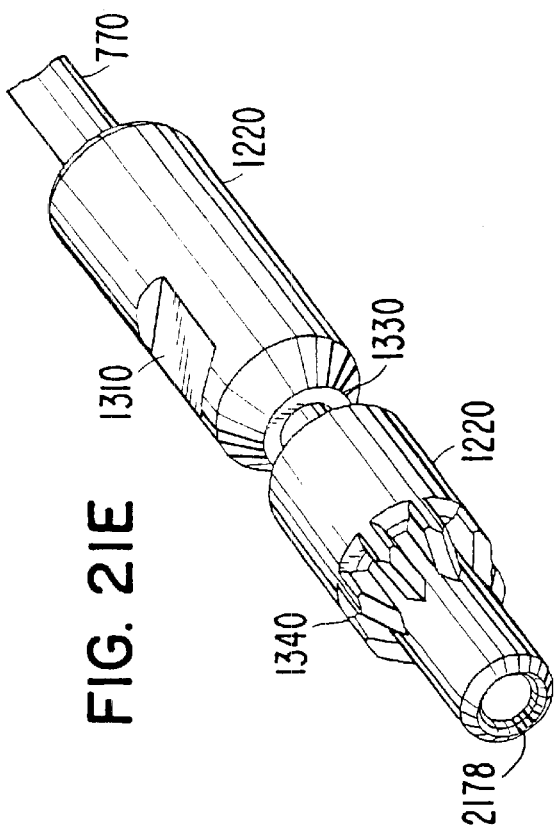

NEEDLE HUB FOR MEDICAL INSTRUMENT

RELATED APPLICATIONS

This Application claims priority to U.S. Provisional Application No. 60/281,825, filed Apr. 6, 2001, and U.S. Provisional Application No. 60/205,053, filed May 18, 2000, both of which are incorporated in their entirety herein by reference.

BACKGROUND OF THE INVENTION

1. Field of the Invention

The present invention relates to a medical instrument used to implant seeds, such as radioactive seeds, into a patient's body. In particular, the present invention relates to a needle hub configuration for a medical instrument.

2. Description of the Related Art

For treating prostate cancer, radioactive seeds are provided to various locations within a patient's prostate gland, by way of a medical instrument, also called a seed implantation device. Typically, a base unit which includes an ultrasound unit is used to determine the exact location of the patient's prostate gland with respect to the base unit. The base unit is capable of being moved either towards the patient or away from the patient.

The ultrasound unit includes a probe, which is inserted into the patient's rectum while the patient is lying on his back. A grid template is mounted onto the base unit, whereby the grid template includes a plurality of rows and columns of needle holes in which a needle can be inserted. Typically, the grid template includes a 13 by 13 matrix of needle holes, whereby adjacent holes on a row or a column are spaced 5 mm apart. Every other row is labeled with a number (e.g., 1, 2, etc.) on the grid template, and every other column is labeled with an alphabetic character (e.g., A, B, etc.). There is a direct relation between the centerline axis of the ultrasound probe and the position of the holes of the grid template.

Based on information obtained from the ultrasound unit, a needle is positioned through a particular hole (e.g., B5 hole) on the grid template, and then the needle is inserted into a region within the patient's body in which the prostate gland is located. By using the ultrasound unit, a precise position of the proximal and distal positions (relative to the ultrasound unit) of the prostate gland can be determined and recorded. The distal position (relative to the ultrasound unit) of the prostate gland is also called the "zero retraction point". Once the prostate gland position information is obtained, a seed implantation plan can be determined by a doctor, where the plan corresponds to a sequential process for injecting seeds into particular locations within the patient's prostate gland. Such treatment is generally started by placing the end of the needle (e.g., bevel end of a bevel needle or the end of a trocar needle) at the zero retraction point, and then start applying seeds with respect to that reference point.

For a conventional seed implantation device, a needle is first placed into a particular needle hole of a grid template, and then the seed implantation device is held in place by a doctor and attached to the needle. The seed implantation device is then used to inject one or more seeds into the patient's body through the needle. When finished with that hole, the seed implantation device is detached from the needle, and placed aside. Then, the needle is removed from the grid template, and a new needle is positioned at another needle hole of the grid template, according to the specific plan for treating the patient's prostate gland. Alternatively, some physicians prefer to insert an entire row of needles onto the grid template, and thereby move from needle to needle. Other physicians implant all needles required at the deepest depth position, and then continue with all needles required at the next-deepest depth position, and so forth. One conventional seed implantation device is called a MICK applicator, and requires the operator to physically reposition the MICK applicator back onto a new needle positioned onto the grid template. Such an applicator is described in U.S. Pat. No. 5,860,909, entitled Seed Applicator for Use in Radiation Therapy.

As described above, the needle is attached to the medical instrument, and in particular, to a distal end of the medical instrument. The coupling of the needle to the medical instrument is an important element in being able to properly implant seeds into a patient.

SUMMARY OF THE INVENTION

One object of the present invention is to provide a needle hub configuration, whereby a needle can be attached to the medical instrument in a fairly easy manner, and also allow for proper orientation of the needle to be able to implant seeds properly.

This object may be achieved by an apparatus for coupling a needle to a medical instrument. The apparatus includes a needle hub that is coupled to the needle, the needle hub having a plurality of cam registration ribs on an outer surface thereof. The apparatus also includes a needle cam that has a plurality of hub registration ribs on an inner surface thereof. The apparatus further includes a needle nozzle disposed at a distal end of the medical instrument, the needle nozzle being configured to hold the needle cam in place within the needle nozzle. The cam registration ribs are fitted between the hub registration ribs to provide a coupling of the needle to the medical instrument.

The above-mentioned object may also be achieved by an apparatus for coupling a needle to a medical instrument. The apparatus includes needle hub means for attaching to a proximal end of the needle. The apparatus further includes needle cam means for accepting the needle hub means for coupling thereto. The needle cam means is disposed in a frame of the medical instrument at a distal end thereof.

The above-mentioned object may also be achieved by a method for coupling a needle to a medical instrument. The method includes a step of attaching a needle hub to the needle, the needle hub including first registration ribs on an external surface thereof. The method also includes a step of registering the first registration ribs of the needle hub with second registration ribs on an inner surface of a needle cam disposed on a distal frame portion of the medical instrument. The needle hub is coupled to the needle cam as a result, thereby coupling the needle to the medical instrument in a non-integral manner.

BRIEF DESCRIPTION OF THE DRAWINGS

The invention will become more fully apparent from the following detailed description when read in conjunction with the accompanying drawings with like reference numerals indicating corresponding parts throughout, and wherein:

FIGS. 17A through 17G show various views and cross sections of the needle spin assembly and needle coupling assembly, according to an embodiment of the present invention;

FIGS. 21A, 21B, 21C, 21D and 21E show top, side, front, back and perspective views, respectively, of the needle assembly, according to an embodiment of the present invention;

FIGS. 23A through 22F show various views of the collar that is used to cause the needle assembly to spin (when the collar is disposed within slots of the needle cam and moved), according to an embodiment of the present invention.

DETAILED DESCRIPTION OF THE PREFERRED EMBODIMENTS

Preferred embodiments of the present invention will be described in detail hereinbelow, with reference to the drawings.

The present invention is directed to a medical instrument, more particularly, a seed implantation device, which is configured so that it can be coupled to a targeting fixture for attachment to a needle positioned through a needle hole on a grid template. The medical instrument is also configured to receive a seed cartridge, and to remove a seed from the seed cartridge in order to provide the seed to a needle that can be attached to a front portion of the medical instrument. Details of the targeting fixture on which the medical instrument can couple to, more particularly, to a cradle unit or a sheath unit of the targeting fixture, is a subject of a first related application entitled "TARGETING FIXTURE", Provisional Application Serial No. 60/205,094, filed May 18, 2000, a second related application entitled "TARGETING FIXTURE TO A GRID TEMPLATE", Provisional Application Serial No. 60/205,054, filed May 18, 2000, and a third related application entitled "GRID SHEATH FOR MEDICAL INSTRUMENT", Provisional Application Serial No. 60/265,075, filed Jan. 31, 2001, each of which is incorporated in its entirety herein by reference. Details of the seed cartridge is a subject of a fourth related application entitled "CARTRIDGE-MOVEABLE SHIELD", Provisional Application Serial No. 60/205,055, filed May 18, 2000, which is incorporated in its entirety herein by reference. Seeds within the cartridge are capable of being examined for potency, by using a device called a well chamber holder, which is the subject of a fifth related application entitled "WELL CHAMBER HOLDER", Provisional Application Serial No. 60/205,298, filed May 19, 2000, which is incorporated in its entirety herein by reference.

Figure 10:
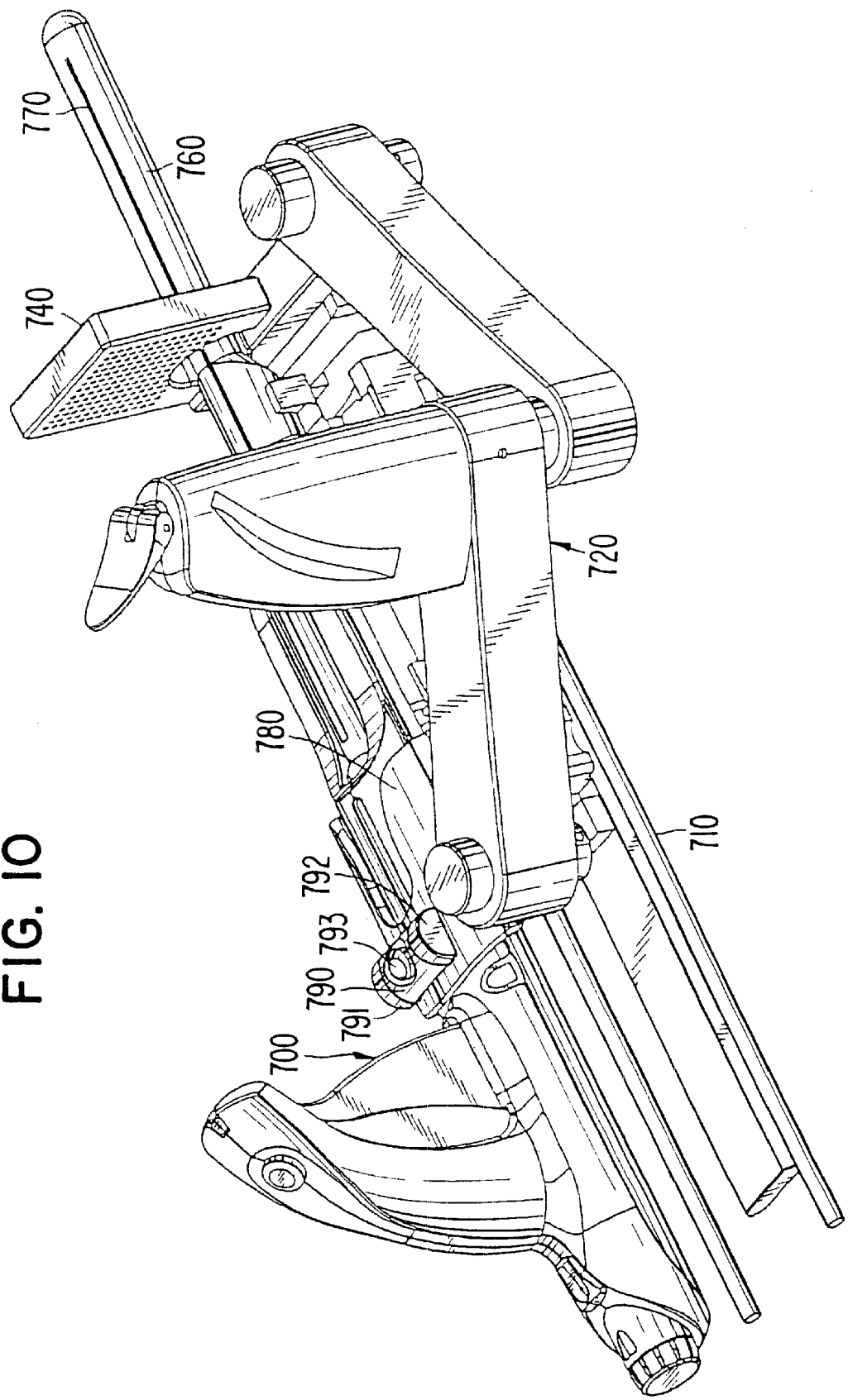
FIG. 10 shows a medical instrument in accordance with the present invention, coupled to a sheath unit of a targeting fixture.

FIG. 10 shows a medical instrument 700 in accordance with the present invention, which is coupled to a sheath unit 780 of a targeting fixture 720. The sheath unit 780 allows the medical instrument 700 to be fitted into place at a proper x, y, z location (or x, y location, depending upon which type of targeting fixture is used) with respect to a grid template 740, and also allows for the medical instrument 700 to be attached to a needle (also called a "needle cannula"hereinbelow) 770 placed into a particular hole of the grid template 740. Alternatively, the medical instrument may be coupled to a sheath unit as described in the third related application, whereby a distal end of that sheath unit is pushed against the grid template to thereby maintain the medical instrument in place (with the medical instrument coupled to the sheath unit frame) to allow for a medical procedure to take place.

Figure 1:
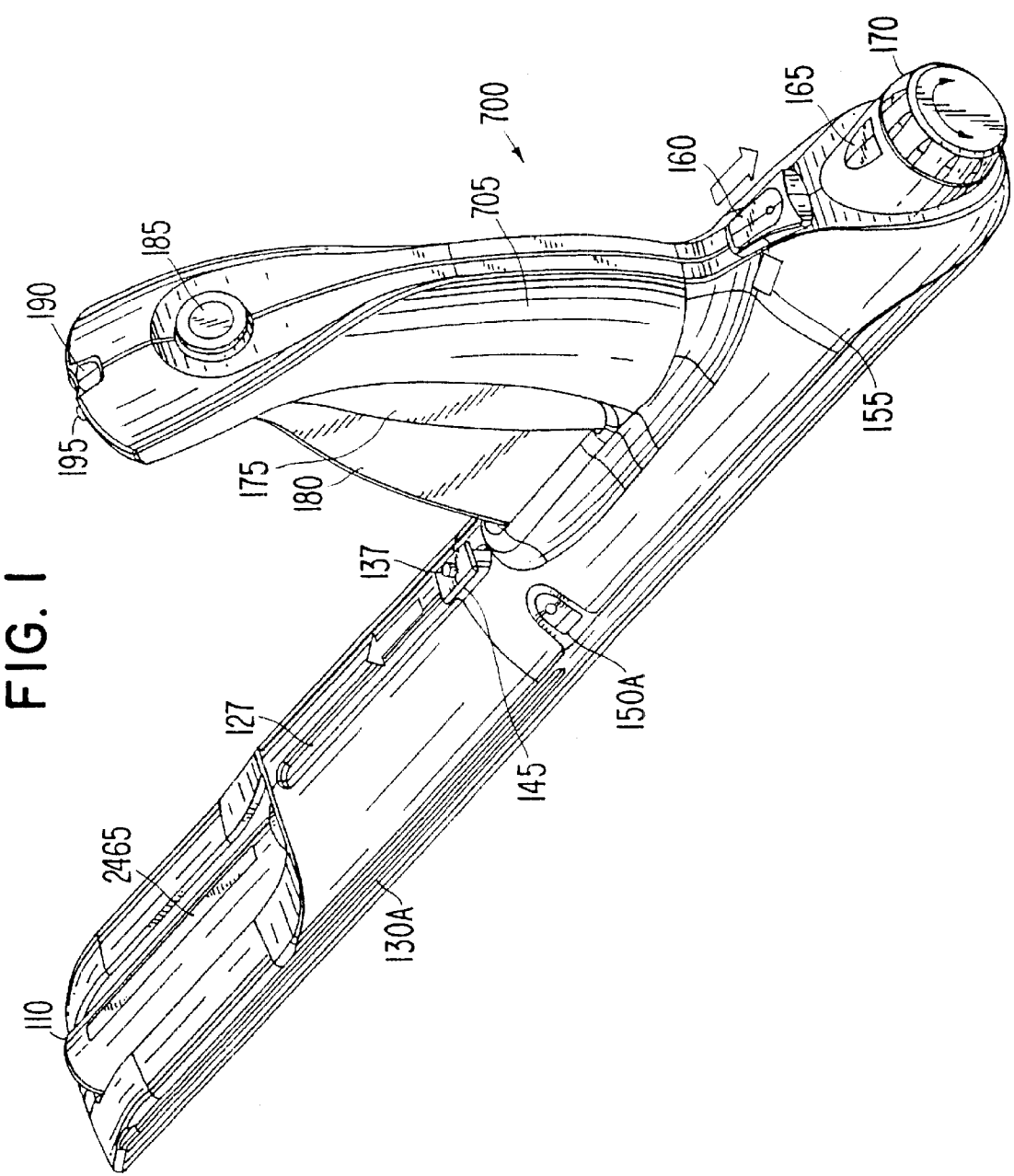
FIG. 1 shows a top perspective view of the medical instrument, which has housed within it a seed cartridge at a front portion of the medical instrument, according to the invention.
Figure 2:
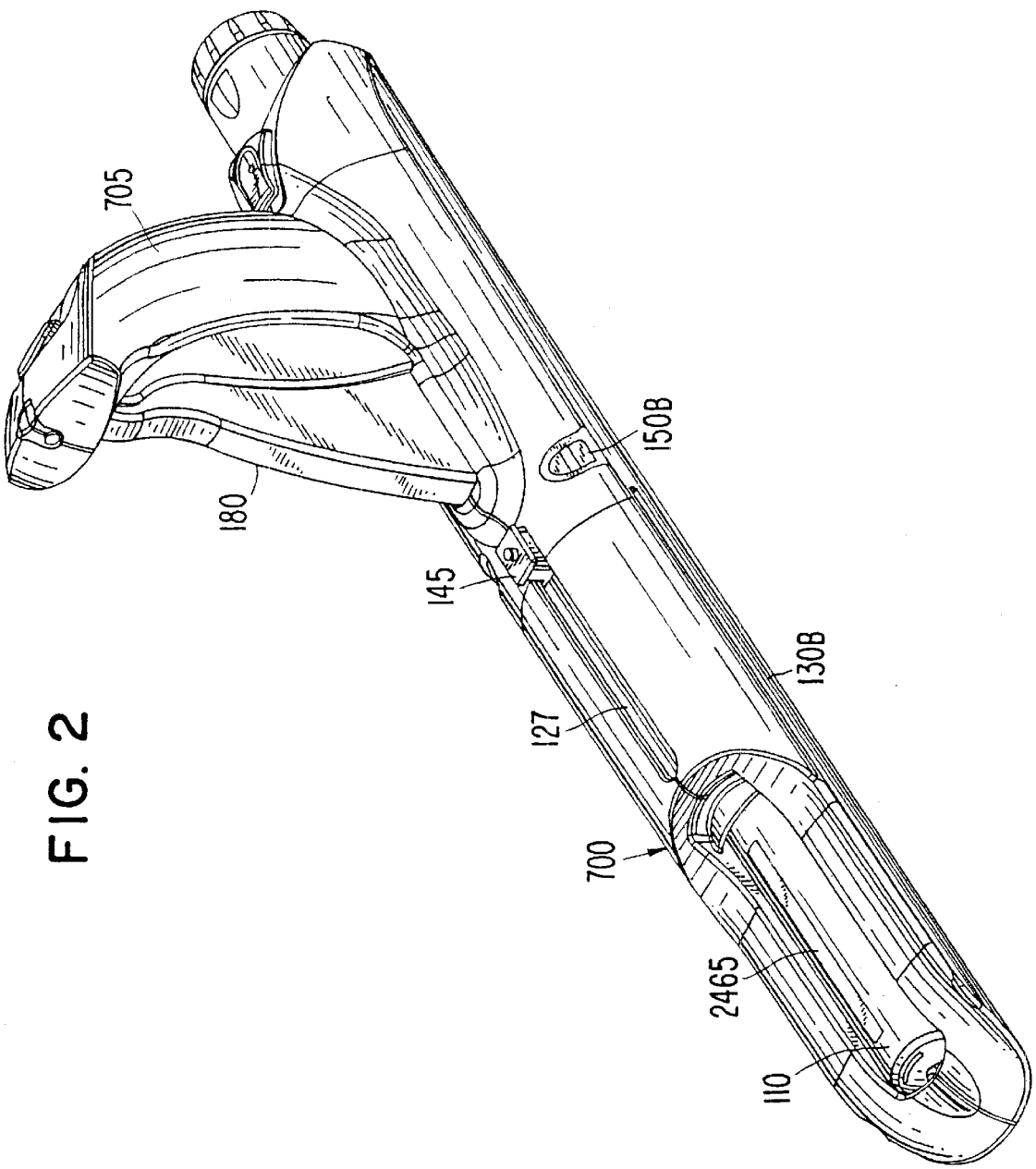
FIG. 2 shows a different top perspective view of the medical instrument, which has housed within it a seed cartridge at a front portion of the medical instrument, according to the invention.
Figure 3:
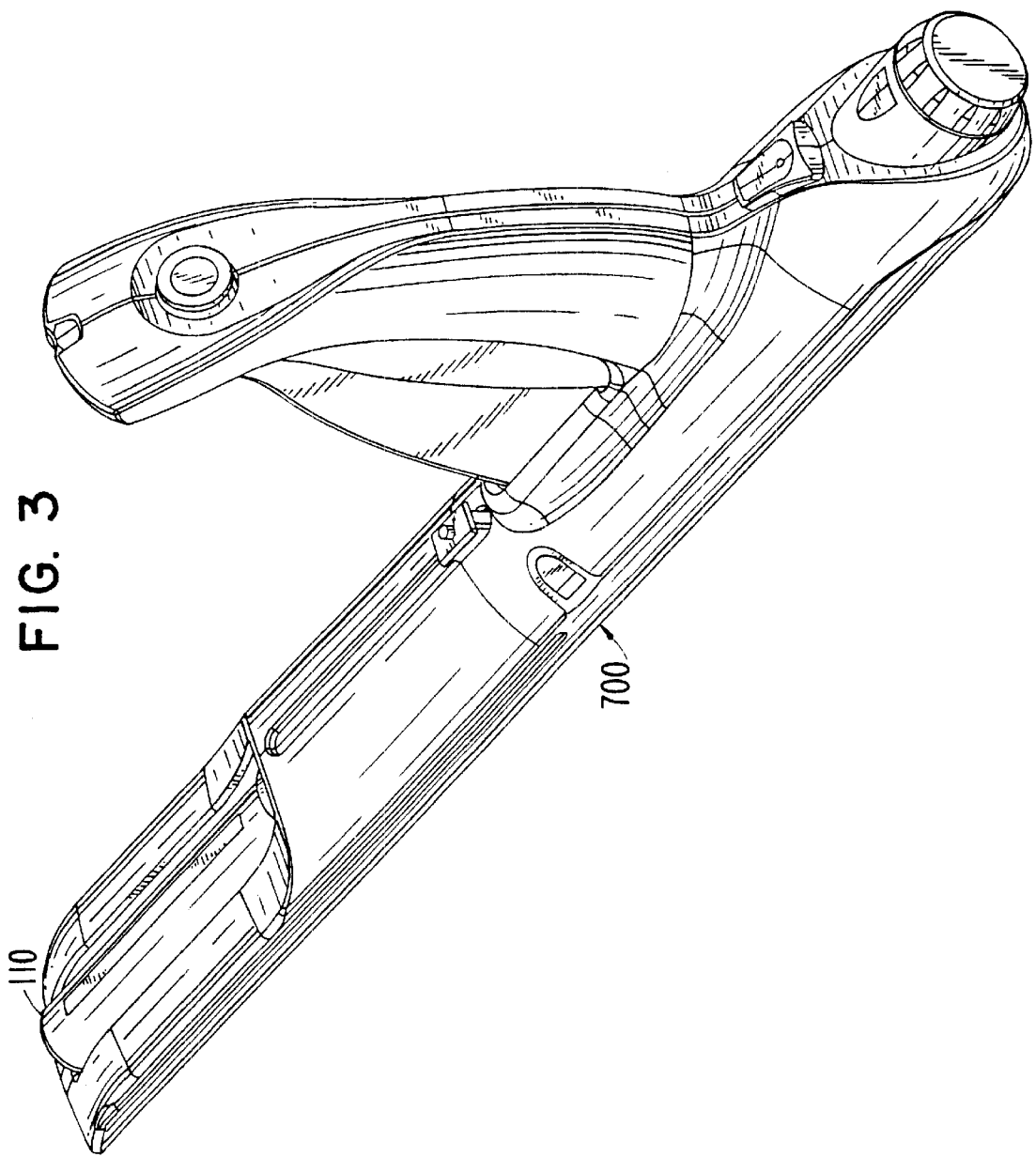
FIG. 3 shows yet another different top perspective view of the medical instrument, which has housed within it a seed cartridge at a front portion of the medical instrument, according to the invention.
Figure 4:
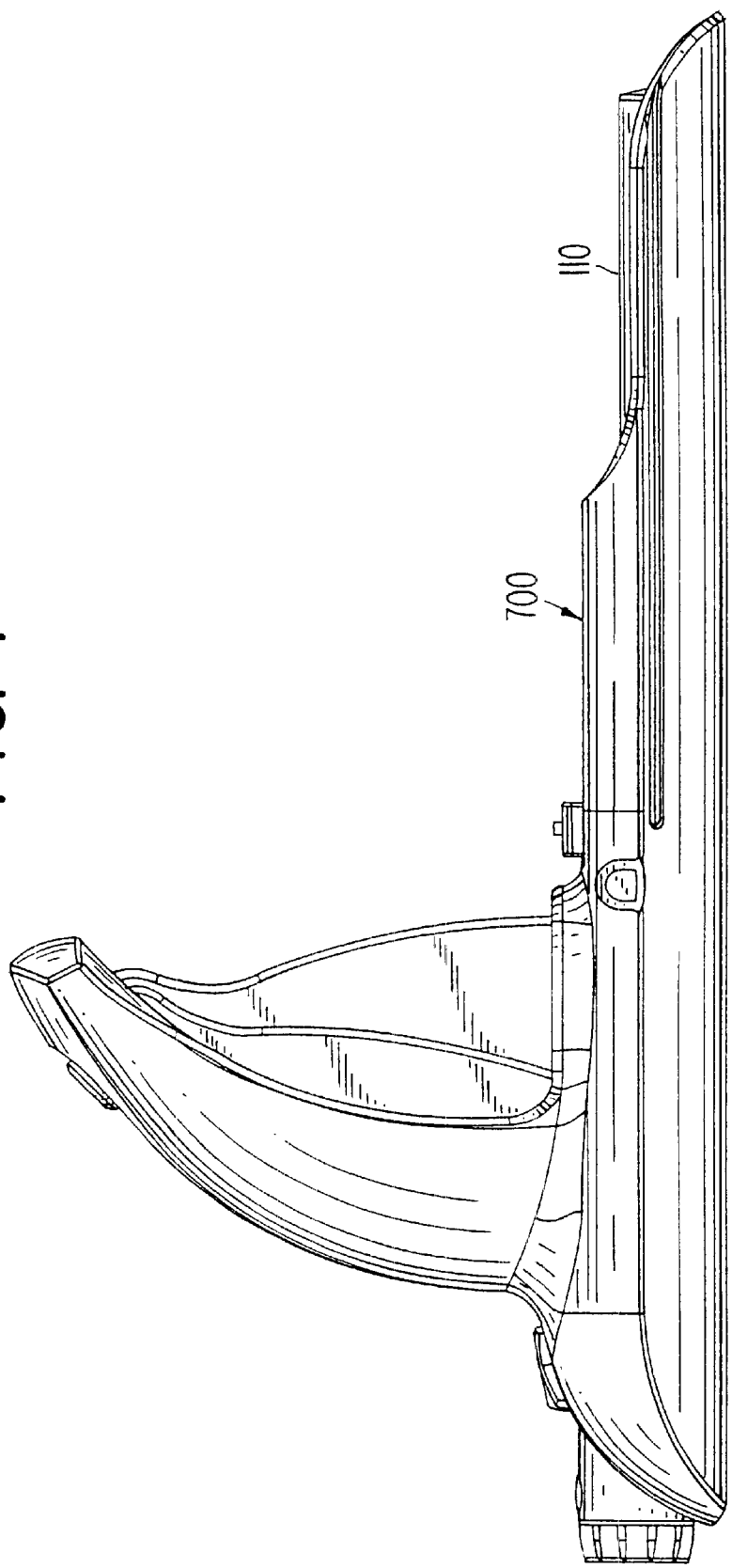
FIG. 4 shows a side view of the medical instrument, which has housed within it a seed cartridge at a front portion of the medical instrument, according to the invention.
Figure 5:
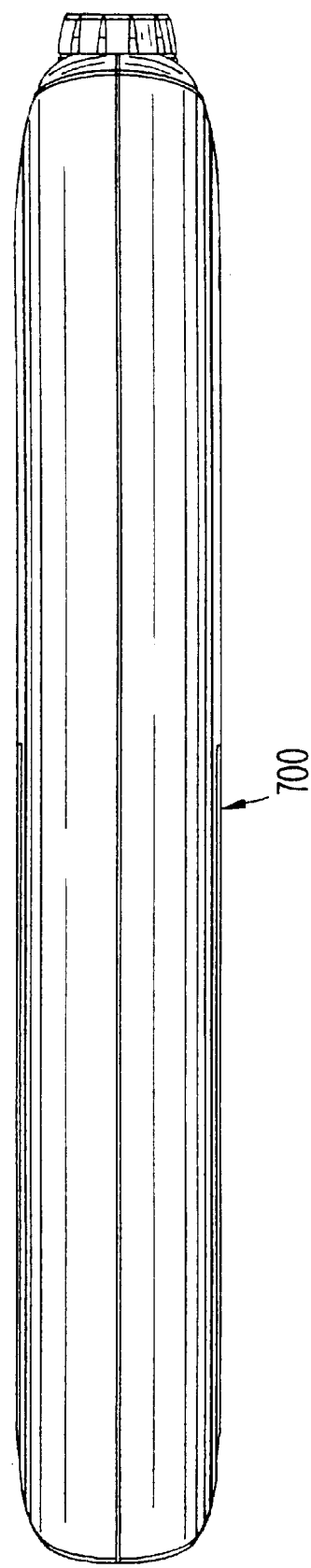
FIG. 5 shows a bottom view of the medical instrument, according to the invention.
Figure 6:
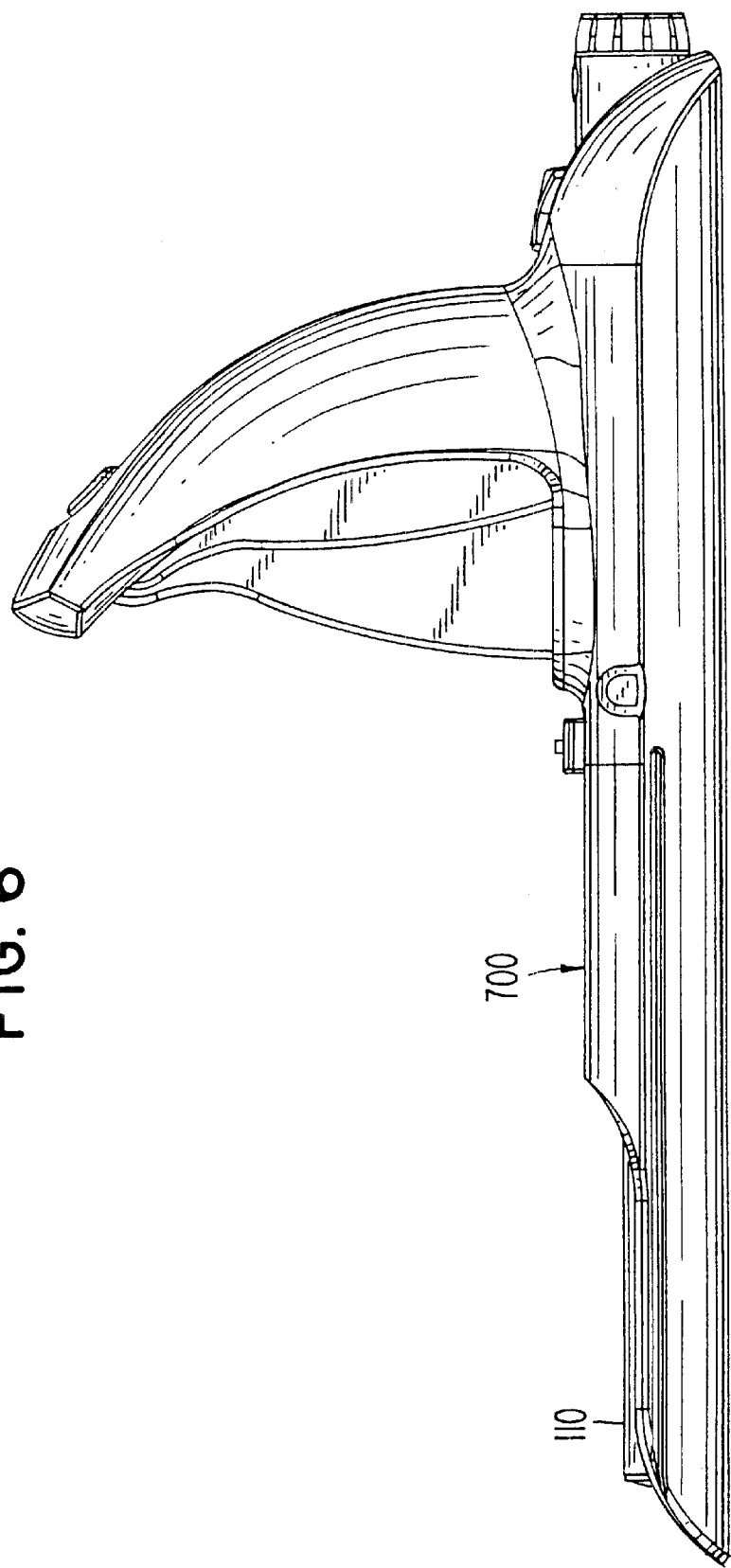
FIG. 6 shows the opposite side view, with respect to the view of FIG. 3, of the medical instrument, which has housed within it a seed cartridge at a front portion of the medical instrument, according to the invention.
Figure 7:
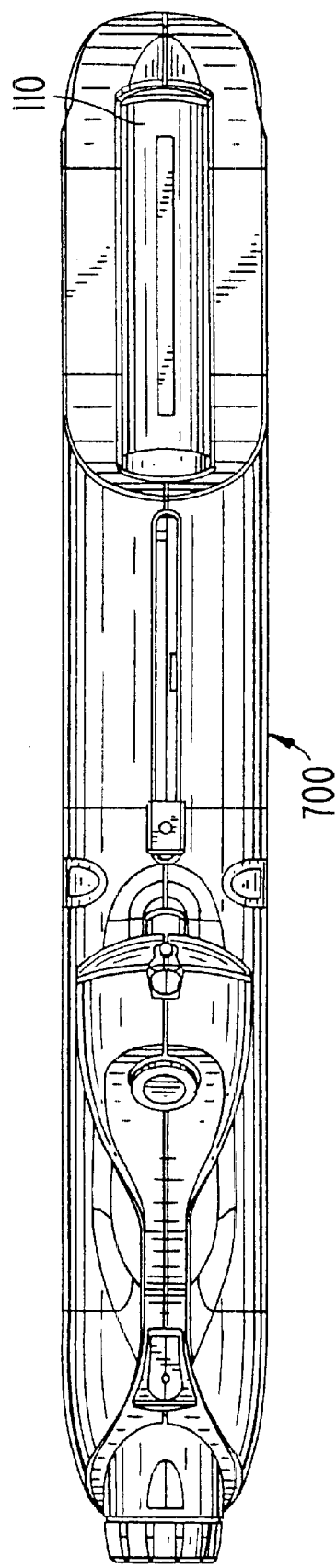
FIG. 7 shows a top view of the medical instrument, which has housed within it a seed cartridge at a front portion of the medical instrument, according to the invention.
Figure 8:
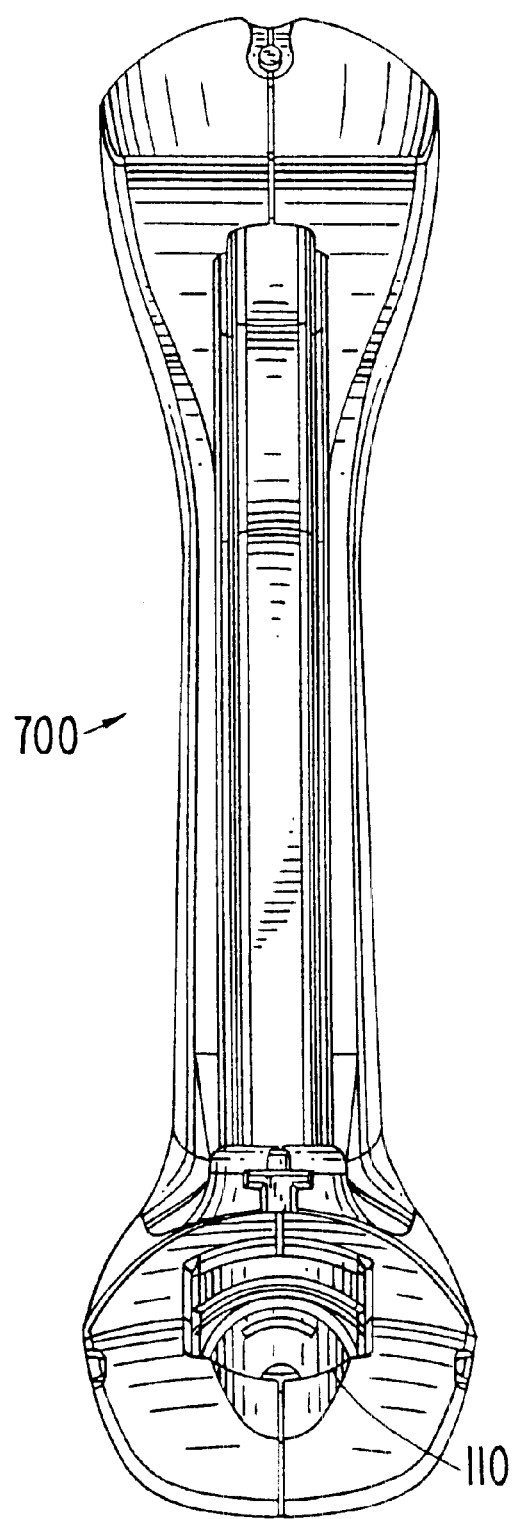
FIG. 8 shows a front view of the medical instrument, which has housed within it a seed cartridge at a front portion of the medical instrument, according to the invention.
Figure 9:
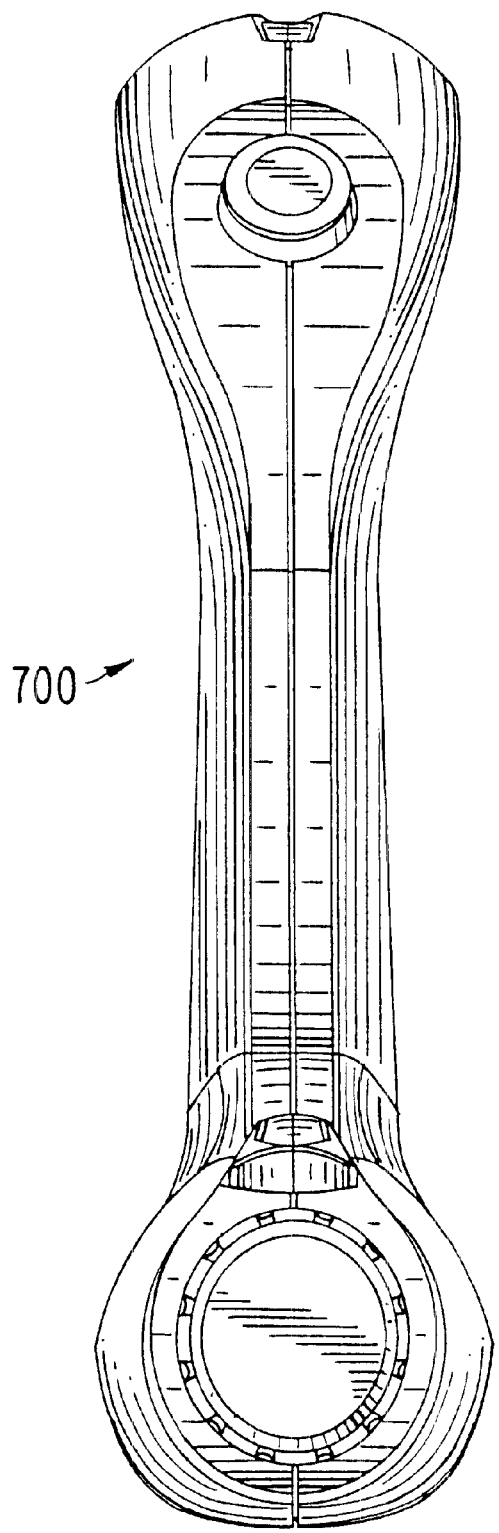
FIG. 9 shows a back view of the medical instrument, according to the invention.

Referring back to FIG. 10, the sheath unit 780 includes slots (not shown, but see the description in the first and second related applications). A key way (not shown, but see the related applications) is respectively provided in each of the slots. Each key way is preferably a lubricated plastic part, and juts out of its respective slot in order to engage with a sheath interface slot 130A, 130B provided on opposite sides of the medical instrument 700. FIGS. 1 and 2 show the slots 130A, 130B on the sides of the medical instrument 700. The key ways of the sheath unit 780 are held in place within the slots of the sheath unit 780 by way of set screws, which are screwed in via screw holes on the sheath unit 780.

Referring back to FIG. 10, the sheath unit 780 has a U-shaped opening at its top portion. The length of this U-shaped opening is preferably sized to allow an operator to discern the seed count indicator located on the cartridge. The sheath unit 780 has a cylindrical element 790 that is fitted onto its top portion. The cylindrical element 790 is fitted with first and second side buttons 791, 792 and a top button 793. The functions of these buttons will be explained later. In short, the first and second side buttons 791, 792 are simultaneously (or individually, in an alternative configuration) engaged by pushing both (or at least one, in the alternative configuration) of them inwards. This action allows a nut box interface 145 disposed on the top of the medical instrument 700 to move relative to the medical instrument 700. The nut box interface 145 can be seen in FIGS. 1 and 2. The nut box interface 145 couples to an element (not shown) on the bottom of the upper surface of the sheath unit 790, below the buttons 791, 792, 793.

When the targeting fixture 720 is placed into its proper position with respect to the grid template 740, the medical instrument 700 can be inserted and held in place within the sheath unit 780. The side slots 130A, 130B of the medical instrument 700 are fitted onto the key ways of the sheath unit 780, and the medical instrument 700 is pushed in a direction towards the grid template 740. The medical instrument 700 is locked in place when the nut box interface 145 couples to the element on the bottom of the upper surface of the sheath unit 780. In the preferred embodiment, a clicking sound is heard at that time, informing the user that the medical instrument 700 is correctly positioned within the sheath unit 780.

The medical instrument 700 is also positioned so as to be engaged with the needle 770. The precise coupling of the needle 770 to the medical instrument 700 will be described in detail in a later section. In particular, a needle hub and a needle cam will be described, each having registration ribs for coupling to each other and each being disposed within a distal frame portion of the medical instrument, to provide coupling of the needle 770 to the medical instrument 700.

When the top button 793 disposed on the cylindrical element 790 of the sheath unit 780 of FIG. 10 is pushed downwards from its normal, upwards position, the nut box interface 145 of the medical instrument 700 disengages from the sheath unit 780, thereby allowing the medical instrument 700 to be freely moved by sliding it back out of the sheath unit 780. That way, the medical instrument can be slid out of the sheath unit 780.

Figure 11:
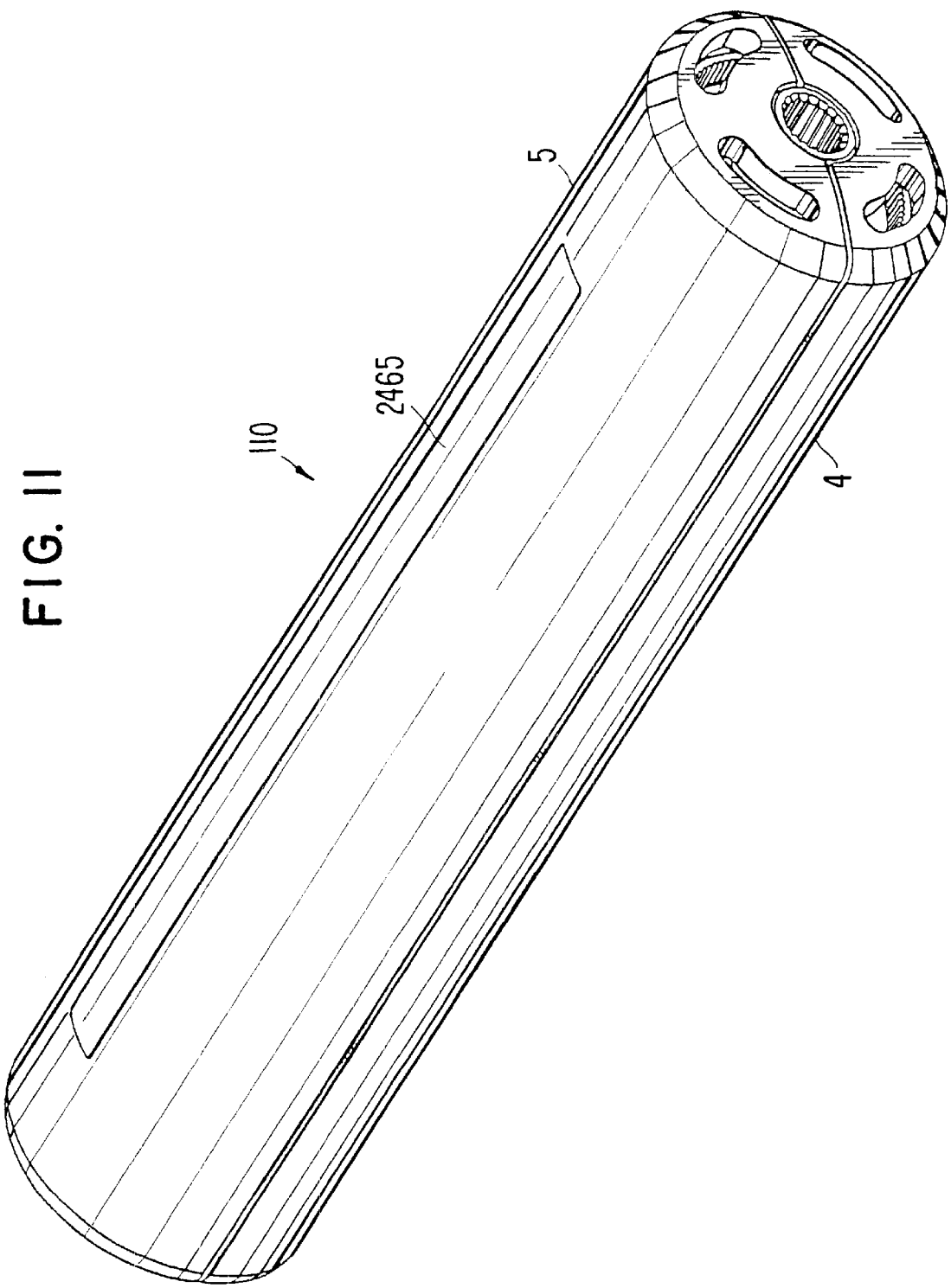
FIG. 11 shows a cartridge that can be inserted into the medical instrument, according to the present invention.

Referring now to FIGS. 1–10, which show views from different angles, the medical instrument 700 includes a handle 705 which has an actuator/trigger 180 by which a user can push inwards to eject a seed out of the medical instrument 700 and into a needle 770, and thereby into a patient. The medical instrument 700 is shown as having a cartridge accepting region for accepting a seed cartridge 110 that contains seeds. The cartridge accepting region is located at a distal portion of the medical instrument 700 adjacent to the location where the needle 770 is coupled to the medical instrument 700. The cartridge 110, which includes a seed capacity indicator (not shown) located underneath the lens 2465, is the subject of the CARTRIDGE-MOVEABLE SHIELD related patent application, referred to previously. The seed cartridge 110 is shown by itself in FIG. 11.

As a seed is fired from the medical instrument 700 and into a patient by way of the needle 770, the medical instrument 700 backs out from the sheath unit 780 in a direction away from the grid template 740. In more detail, as the trigger/actuator 180 on the handle 705 of the medical instrument 700 is engaged by a predetermined amount from its home position (e.g., approximately one-half the maximum allowable stroke of the trigger 180 on the handle 705), a seed is removed from the seed cartridge 110 by the medical instrument 700, and the seed is pushed into the needle 770 by way of a pusher, or stylet, located within the housing of the medical instrument (not shown in FIGS. 1–10). As the user continues to engage the trigger mechanism 180 past the predetermined amount to its fully engaged position, the medical instrument 700 moves back away from the grid template 740, but remains coupled to the sheath unit 780.

In more detail, the medical instrument 700 moves backwards in a direction away from the grid template 740 (and thereby away from the patient), while still seated in the sheath unit 780. This occurs due to the nut box interface 145 moving from its initial location at its most proximal position, to a position that approaches the distal end (the end at which the needle is attached) of the medical instrument 700. In other words, as the trigger/actuator 180 is actuated to move the medical instrument 700 back away from the grid template 740, the nut box interface 145, which is grabbed by an element on the bottom surface of the sheath unit 780, is held in a fixed position with respect to the sheath unit 780, while the rest of the medical instrument 700 moves backwards with respect to the sheath unit 780. In FIGS. 1 and 2, the nut box interface 145 is shown at its most proximal position on the medical instrument 700.

The nut box interface 145 is capable of movement longitudinally within the slot 127 in which it is disposed on the top side of the medical instrument 700, as seen best in FIGS. 1 and 2. The slot distance is approximately the depth of a largest prostate gland (e.g., 3"). The maximum stroke of the medical instrument 700 is determined by this slot distance. Once the medical instrument 700 has moved the entire distance of the slot 127, the nut box interface 145 cannot move any further (since it abuts against the distal end of the slot 127), and the medical instrument 700 has to be reset back into its "zero"or "home" position within the sheath unit 780. The resetting is by way of a user pushing against the first and second side buttons 791, 792 in FIG. 10, which releases the nut box interface 145 from a drive screw (an internal component of the medical instrument to which the nut box interface 145 rides along and can be decoupled from) of the medical instrument 700 to which it is normally attached, thereby allowing a user to slide the medical instrument 700 within the sheath unit 780 back to a next seed implantation "zero retraction point"position with respect to the grid template 740. When the first and second side buttons 791, 792 are released, the nut box interface 145 re-engages with the drive screw 1210.

At the proximal end of the medical instrument 700 of FIG. 1 is a pitch adjustment knob 170, which can be set to a position to move the medical instrument 700 backwards by a desired amount between consecutive seed implant locations. The pitch adjustment knob 170 may be moved from position to position between seed firings, based on a particular plan that is adopted to treat a patient. A pitch indication window 165 is provided near the pitch adjustment knob 170, to provide a visual indication to the user of the currently-selected pitch amount.

Also shown in FIGS. 1 and 2 is a vernier feature 150A, 150B provided on each side of the medical instrument 700. The vernier feature 150A, 150B informs a user as to the exact z-position during a seed-implanting process. In more detail, the vernier feature 150A, 150B corresponds to a 0 to 3" (or 0 to 80 mm) scale provided on both sides of the medical instrument 700, whereby a window slides over a particular numeric indicator on that scale to inform the user as to the depth of the needle 770 with respect to the proximal and distal ends of the prostate gland. In other words, the vernier feature 150A, 150B informs that user as to how far in the z-direction the medical instrument 700 has moved with respect to the zero retraction point. FIG. 1 shows the vernier feature 150A in the home, or "0", position.

FIG. 1 also shows a seed counter indicator 190 provided at a top portion of the handle 705, and which counts the number of seeds that have been fired. A counter reset button 195 is provided near the seed counter indicator 190, and when pushed resets the count to "0". The count reset feature may also (or alternatively) be coupled to the motion of the needle release handle 160.

Also shown in FIG. 1 is a cosmetic flapper 175, which defines the handle position at the onset of the medical instrument indexing or movement. Thus, as the handle is moved from its unengaged position to the position corresponding to the location cosmetic flapper 175, the medical instrument 700 has not moved as yet. When the handle is moved further inwards, thereby causing the cosmetic flapper 175 to move with it, the medical instrument 700 moves (or indexes).

The nut box interface 145 is shown as having a nut box release trigger 137, which releases the nut box interface 145 from the drive screw when engaged. The nut box release trigger 137 is actuated when the first and second side buttons 791, 792 on the sheath unit 780 are engaged.

At the back portion of the medical instrument 700 there is disposed a needle release 160, which releases the needle 770 from the medical instrument 700. There may also be provided a second needle release on a front portion of the medical instrument 700. FIG. 1 also shows a seed transfer command button 185, which causes a seed to be transferred from the seed cartridge 110 to the medical instrument 700, by causing a seed within the seed cartridge to be placed within a shuttle and to cause the shuttle to extend from the cartridge, with the seed in place within a seed-accepting-hole of the shuttle.

As an optional feature, the medical instrument 700 may include a nut box "not home" warning indicator, which provides a warning indication when the nut box interface 145 is not in the "home"position.

Now, a description will be made with regards to a needle within a patient's body, and the effects of the needle movement on one or more seeds already implanted in the patient's body.

When the medical instrument is first inserted within the patient, the needle 770 is fixed in position, so that the needle 770 is pointed straight into and through the patient's skin, directly along an axis in which the medical instrument 700 is being moved. The coupling of the needle 770 to the medical instrument 700 is by way of a needle hub configuration at a distal end of the medical instrument 700. When the needle 770 is positioned at the proper depth within the patient (e.g., at the proper location for initially depositing seeds into the prostate), the operator activates a button 185 on the medical instrument 700, in order to provide a seed (obtained from the seed cartridge 110 housed within the medical instrument) to the patient's prostate, by way of the needle 770.

Once a first seed or first group of seeds are deposited at the initial, furthest-depth position within the patient's prostate gland, the medical instrument 700 is moved, so as to inject a next seed or group of seeds at a position in the prostate gland that is closer to the point at which the needle 770 initially entered the patient's skin. This movement of the medical instrument 700, while it is coupled to the sheath unit 780, is described above with reference to the nut box assembly 145 and its movement within the medical instrument 700.

During the seed implantation procedure, care must be taken that the needle 770 does not go directly back solely in a linear, non-rotated manner from a first seed implantation position to a second seed implantation position. This is the case since such movement tends to cause the seeds deposited in the first position to be sucked, or drawn, towards the second position, as recognized by the inventors. This sucking action is undesirable, and leads to seeds being moved to undesired locations within a patient's prostate. These undesired locations are locations different from where the seeds were initially deposited by way of the needle 770. The exact cause for this sucking action is not completely known, but it is probably due at least in part to the fluid within the patient's prostate gland causing the seeds to be drawn in a direction in which the needle 770 is being drawn, whereby the fluid moves with the needle 770 and creates a linear flow path within the patient's prostate for the seed to move along. In addition, compressed air as a result of seed insertion into tissue, or vacuum caused by needle retraction, may also cause undesired seed sucking action.

The present invention overcomes the problem of improperly disposed seeds, by having the needle 770 swivel, or spin, as the medical instrument 700 is moved directly back away from the patient and in a direction towards the needle insertion point on the patient's skin. By having the needle 770 spin between seed implantation points, the problem due to seeds being drawn towards the withdrawing needle 770 does not occur, at least to the extent that it occurs in conventional procedures that withdraw the needle straight back between seed implantation locations. The spinning action of the needle 770 in accordance with the present invention interrupts the vacuum that is caused when the needle 770 is moved directly back in a linear manner, where this vacuum tends to pull the seeds in a direction in which the needle 770 is being moved to a new seed-implanting location. With the vacuum interrupted, the pull effect on the seeds does not occur, at least to the extent that it would occur if the needle 770 is not spun/swiveled/or rotated between seed implant locations.

Preferably, the needle 770 is locked in place and does not spin or swivel, when the medical instrument 700 (and hence the needle 770 coupled to it) is moved inwards into the patient's body, to a furthest-depth position within inner cavity of the patient. As the medical instrument 700 (and hence the needle 770 coupled to it) is moved back away from the patient, whereby the seeds are implanted at various positions within the prostate gland (from the deepest position to the shallowest position), the needle 770 is caused to spin or swivel, as it is retracted to a new position. The needle 770 spins or rotates when the needle 770 is moved between seed implant locations, while the needle 770 does not spin or rotate at other times.

Also, it is important that the needle 770 be properly coupled to the medical instrument 700, in that the needle 770 does not move from its proper position for implanting seeds. A needle hub configuration, whereby the needle 770 is to be coupled to components at a distal end of the medical instrument 700, is needed to allow such coupling.

Figure 12:
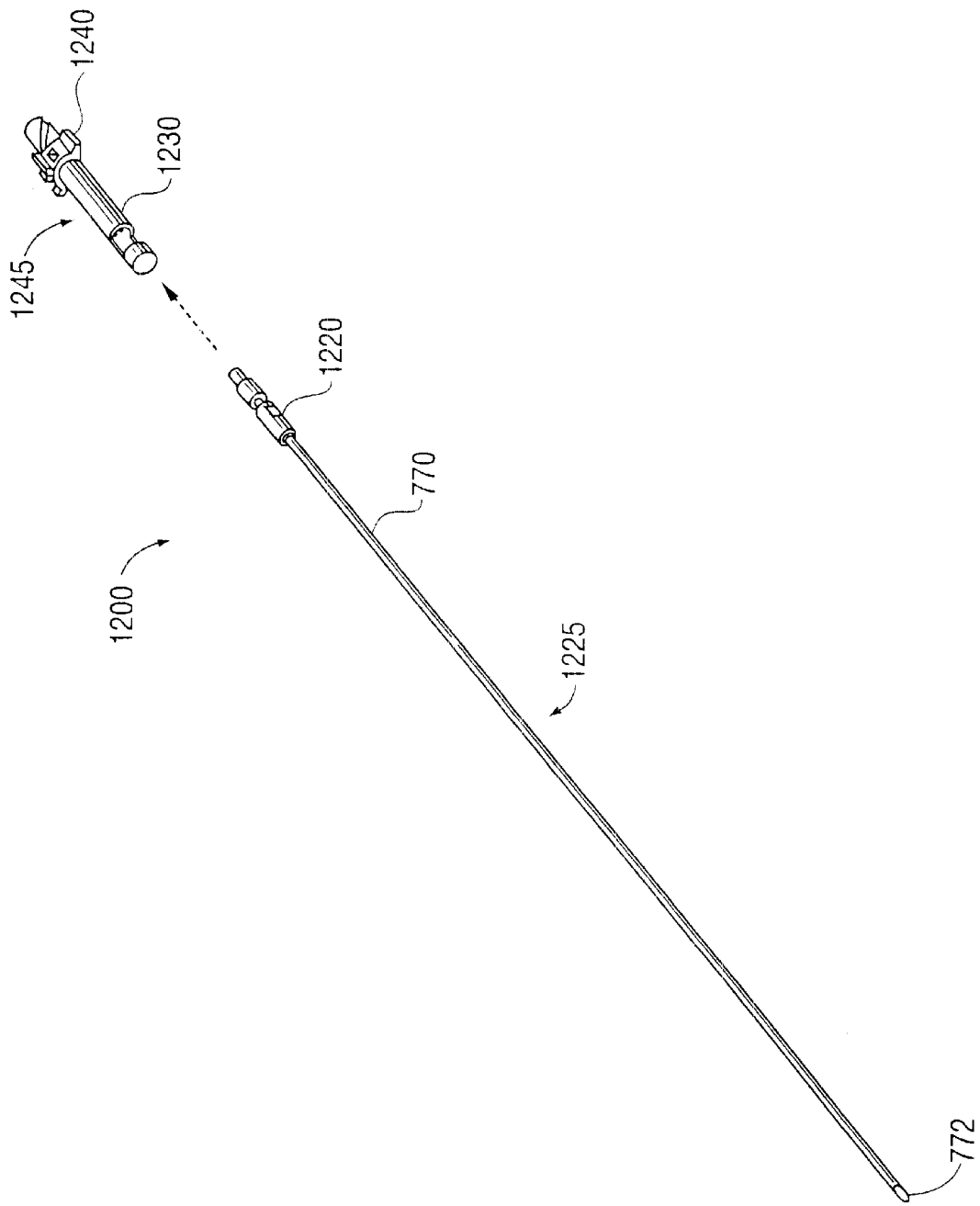
FIG. 12 shows a needle spin mechanism assembly, as well as a needle hub configuration for attaching a needle to a medical instrument, according to an embodiment of the present invention.

FIG. 12 shows a perspective view of various elements in a needle hub assembly 1200. These elements include a needle cannula 770 and a needle hub 1220, which make up a needle assembly 1225. Other elements include a needle cam 1230 and a collar 1240, which provide a needle spin mechanism 1245 for a needle coupled to the medical instrument. The needle hub 1220 and needle cam 1230 make up a needle/medical instrument coupling structure (along with other components, such as a needle retention arm, to be described later on).

The needle hub 1220 is fitted tightly onto the proximal end (that is, the non-beveled end) of the needle cannula 770, whereby the needle hub 1220 cannot be readily removed from the needle cannula 770 without damaging the needle assembly 1225. In essence, the needle assembly 1225 is an integral component, whereby the needle cannula 770 and the needle hub 1220 can be considered to be a one-piece item after a manufacturing process of coupling the needle hub 1220 to the needle cannula 770. The needle hub 1220 is preferably a plastic part, while the needle cannula 770 is preferably a metal part. The needle cam 1230 and the collar 1240 are preferably plastic parts.

Figure 13:
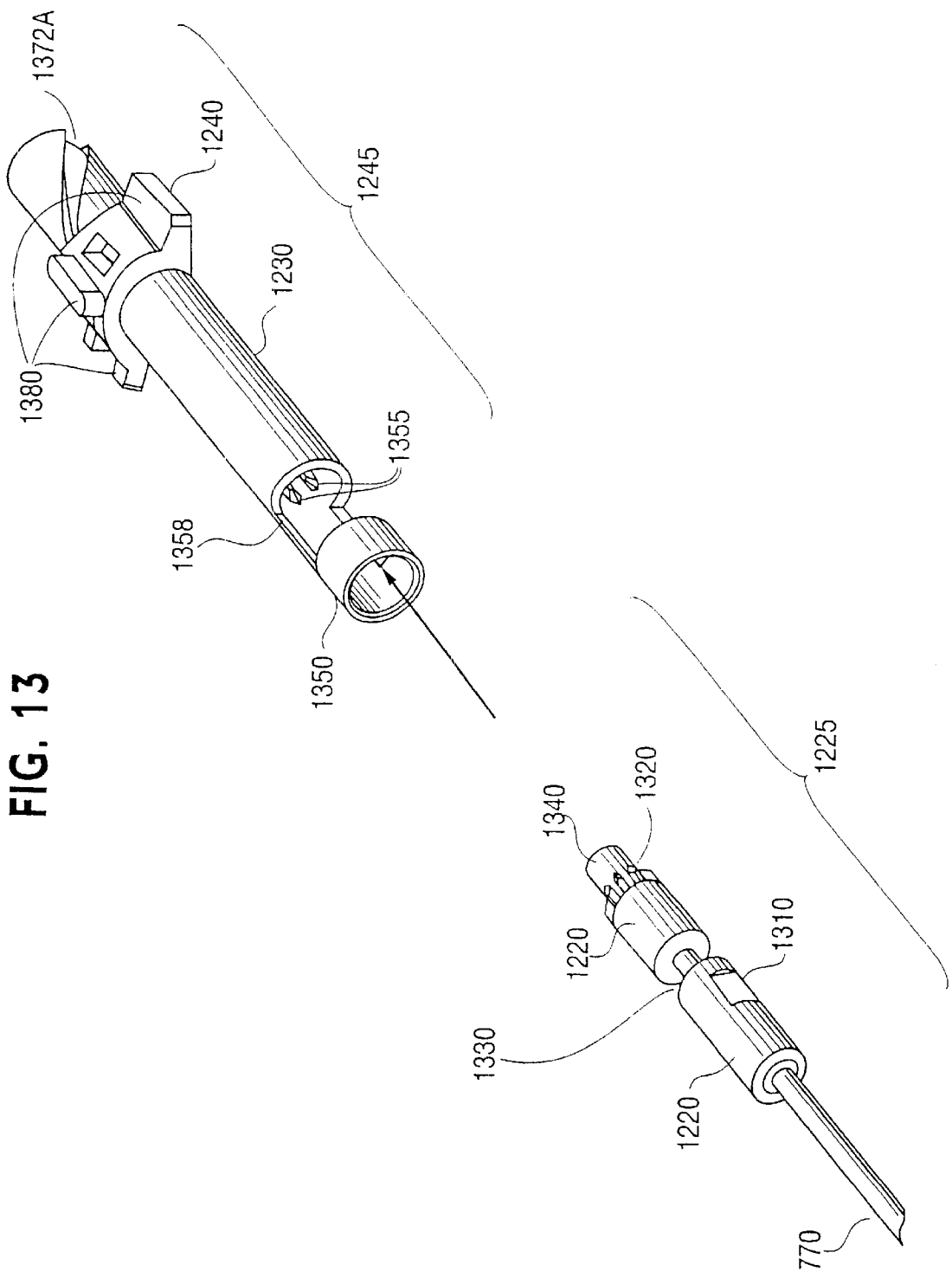
FIG. 13 shows a blow-up of the elements used to couple the needle assembly to the needle cam, so as to provide a coupling of the needle to the medical instrument, according to an embodiment of the present invention.

FIG. 13 is a blow-up view of the proximal end of the needle assembly 1225 and the needle spin mechanism 1245. The needle hub 1220 includes a needle bevel point orientation indicator 1310, a needle release arm retention slot 1330, and needle registration ribs 1340 with rib lead-in chamfers 1320.

The needle cam 1230 includes a needle stabilizer collar 1350, cam registration ribs 1355, and an opening 1358 for a needle release arm 1360. The collar 1240 is configured to move along two cam slots 1372A, 1372B (only one visible in FIG. 13) on the proximal end of the needle cam 1230. The collar 1240 includes anti-rotation ribs 1380, which will be explained in more detail in a later portion of this application.

For performing a medical procedure, the needle cannula 770 may have to be inserted in one of a multitude of angular positions, and the present invention allows for such different angular insertions of the needle cannula 770. The needle registration ribs 1340 on the needle hub 1220 are male protrusions that are received by female features, corresponding to areas between the cam registration ribs 1355, disposed on an inner surface of the needle cam 1230. That way, when the needle hub 1220 is inserted into the needle cam 1230, the needle registration ribs 1340 register with the cam registration ribs 1355.

Due to the chamfers 1320 on the needle registration ribs 1340, the needle hub 1220 can be properly inserted into the needle cam 1230, even if the needle registration ribs (male features) of the needle hub 1220 are not exactly coincident with the corresponding cam registration ribs (female features) of the needle cam 1230. The chamfers 1320 allow the needle assembly 1225 to find the correct orientation when the needle hub 1220 is inserted into the needle cam 1230, to thereby provide registration of the needle registration ribs 1340 with the cam registration ribs 1355 (or more precisely, between adjacent ones of the cam registration ribs 1355).

When bevel-ended needles are utilized, the needle bevel point orientation indicator 1310 provides for the distal end 772 of the needle to be properly oriented during manual insertion into the patient. It provides an orientation indicator for a surgeon who will insert needles into a patient. Alternatively, a trocar needle may be utilized for implanting seeds, whereby the trocar needle would be coupled to the needle hub 1220 to form a needle assembly. In that case, the needle bevel point orientation indicator 1310 is not needed, and the needle hub 1220 would not have such a feature.

Figure 18:
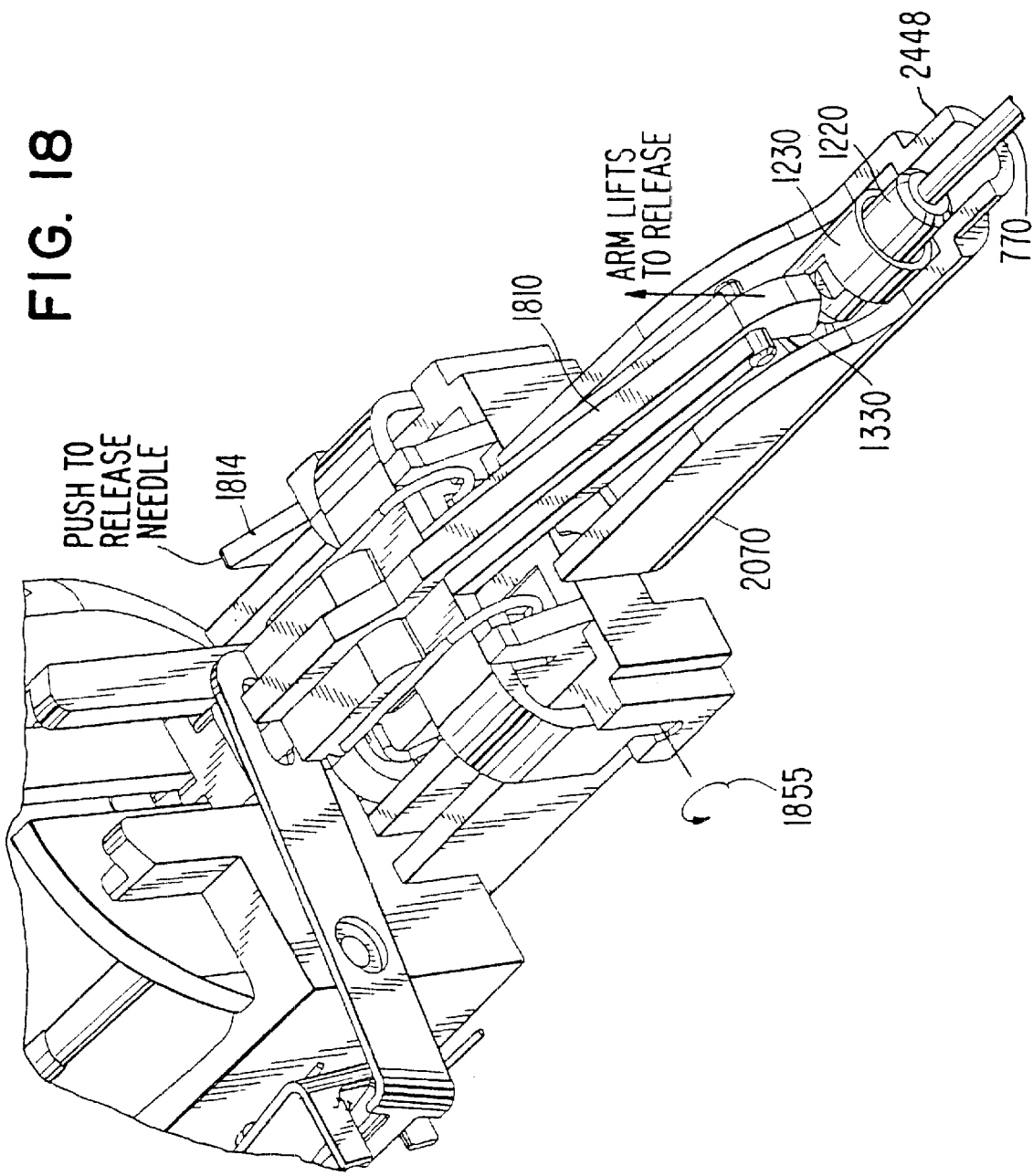
FIG. 18 shows a top perspective view of the needle assembly coupled to a medical instrument, according to an embodiment of the present invention.

The opening 1358 is a region whereby a needle release arm 1810 is disposed, when the needle release arm is in the down position to help hold the needle 770 in place within the distal frame portion of the medical instrument 700. FIG. 18 shows the needle release arm 1810 in the down position, whereby its distal end is disposed within the opening 1358.

When the needle hub 1220 is inserted into the needle cam 1230, the needle release arm 1810 lifts up momentarily (as the proximal portion of the needle hub 1220 is fitted into the needle cam 1230) by riding up over the needle hub 1220 that is being pushed into the needle cam 1230. When the needle assembly 1225 is in place within the needle cam 1230, the needle release arm 1810 drops down to rest within the needle release arm retention slot 1330.

The fitting of the needle registration ribs 1340 between the cam registration ribs 1355 is preferably a "close clearance" fit. By way of example and not by way of limitation, a two to ten thousandths of an inch clearance between the ribs can be provided to provide a proper fit of the needle hub 1220 with the needle cam 1230.

The opening 1358 for accepting the needle release arm 1810 is an opening of 180 degrees (e.g., half-circular region), to allow for a 180 degree rotation of the needle 770 while allowing the needle release arm 1810 to remain in place in the needle release arm retention slot 1330. The opening 1358 is provided so that the needle release arm 1810 will not make contact with the needle cam 1230 during the 180 degree rotation of the needle 770. While the present invention is described with reference to a 180 degree spin of the needle 770, other amounts of spin between seed implant locations may be envisioned, while remaining within the scope of the invention as described herein. For example, a needle spin anywhere from 45 degrees to 720 degrees (or more) may be performed to maintain implanted seeds in place within a patient's body when the needle 770 is moved to a next seed implantation point (or out of the body altogether).

The needle assembly 1225 is caused to spin by movement of the collar 1240, which itself is coupled to the needle cam 1230, whereby the needle cam 1230 is coupled to the needle assembly 1225 (due to the registration of the needle hub 1220 with the needle cam 1230). The collar 1240 has two pins 2310A, 2310B provided on opposite sides of the collar 1240, as seen best in FIGS. 23A, 23B, 23D and 23F. Those pins 2310A, 2310B are respectively engaged into two helical slots 1372A, 1372B that are provided on a proximal end of the needle cam 1230. The collar 1240 rides up and down the needle cam 1230, by way of the pins 2310A, 2310B of the collar 1240 riding along the slots 1372A, 1372B of the needle cam 1230. The slots 1372A, 1372B of the needle cam 1230 are preferably disposed 180 degrees apart from each other, on the proximal end of the needle cam 1230.

Figure 20:
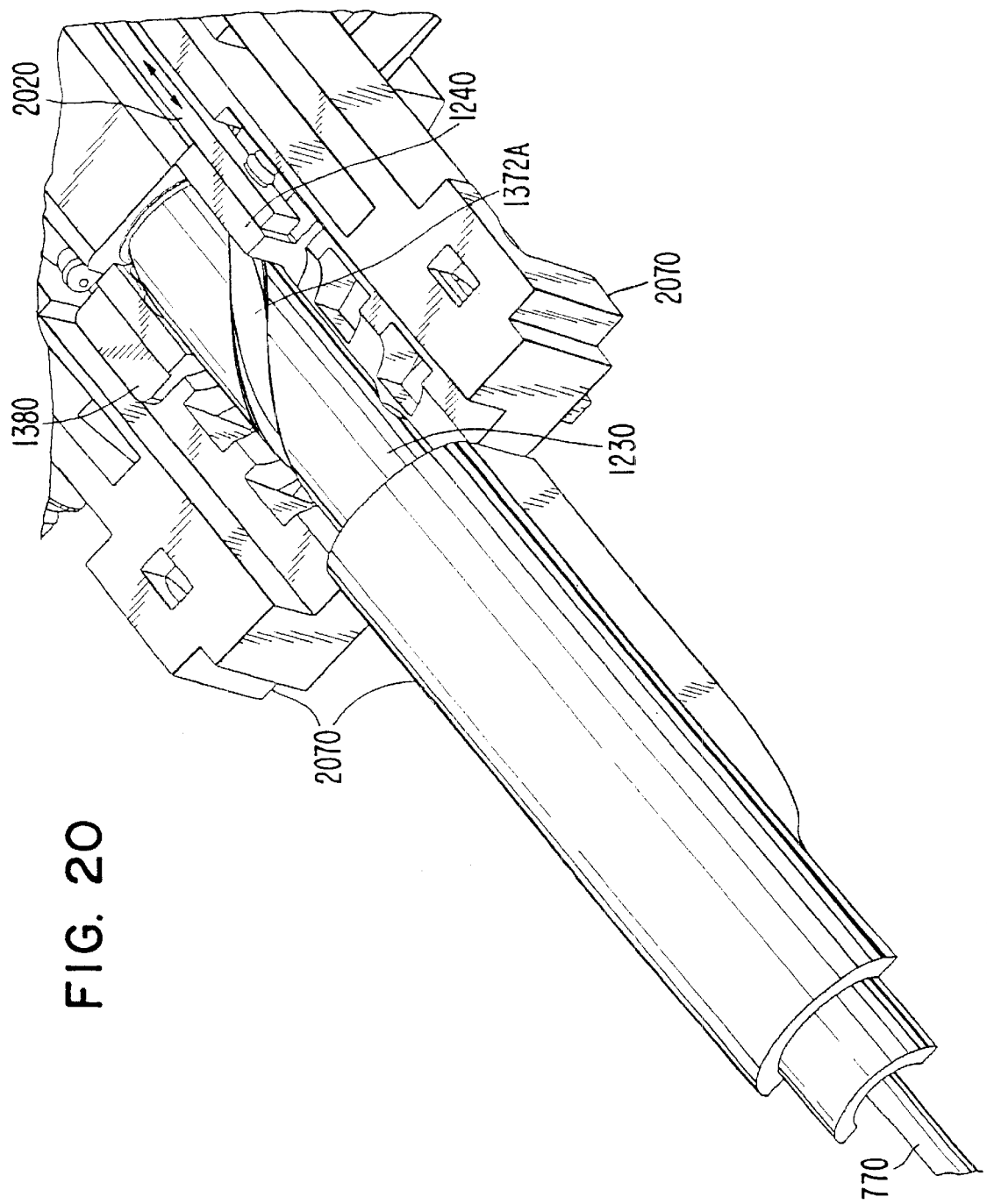
FIG. 20 shows a bottom view of a blow up of a region of the distal frame portion of the medical instrument in which the collar is disposed, whereby the coupling of the collar to a control link is shown, according to an embodiment of the present invention.

FIG. 20 shows a blow up of a portion of a distal frame portion 2070 of the medical instrument 700, which shows the collar 1240 placed into its proper position within the distal frame portion 2070 of the medical instrument 700. A control link 2020 moves in a linear direction as shown by the double-arrow line in FIG. 20, whereby an actuation of the trigger 180 on the medical instrument 700 causes the control link 2020 to move, to create a pulling action on the collar 1240. The collar 1240 is shown in FIG. 20 as being in an actuated position, whereby an action by the operator has caused the control link 2020 to be pulled in a direction towards the medical instrument 700, thereby causing the collar 1240 to be moved in that same direction. The control link 2020 includes a hole at a distal end thereof, whereby a control link attachment pin 2320 of the collar 1240 is fitted through that hole (see FIGS. 23A, 23B, 23D, 23E, 23F). That way, when the control link 2020 is pulled back in a direction towards the medical instrument 700, the collar 1240 is pulled back in that same direction as well.

FIG. 20 also shows the anti-rotation ribs 1380 of the collar 1240, which maintain the collar 1240 in its proper position, and do not allow the collar 1240 to rotate or move in a direction other than a direction in which the control link 2020 moves. FIGS. 23A through 23F show the anti-rotation ribs 1380 on the collar 1240. The collar 1240 is in its resting, or home position, when it is at its most distal position with respect to the medical instrument body. The collar 1240 is shown in its most proximal position in FIG. 20.

Figure 14:
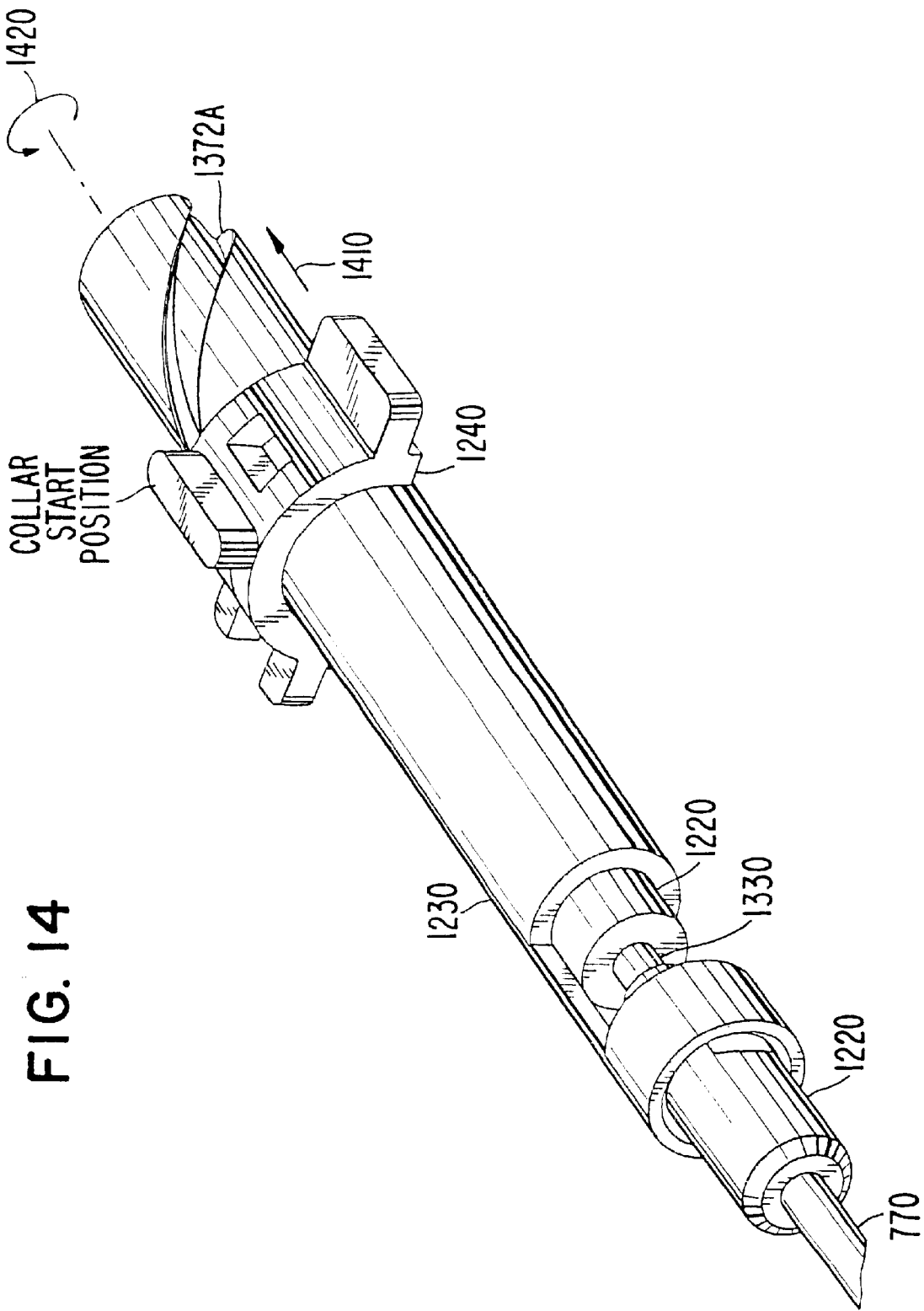
FIG. 14 shows a blow-up of the needle assembly coupled to the needle cam, as well as elements used to cause the needle assembly to spin while being coupled to the needle cam, according to an embodiment of the present invention.

FIG. 14 shows the direction of collar movement, by way of the "collar motion" arrow 1410 provided in that figure. Collar motion in the direction of the collar motion arrow 1410 results in rotation of the needle cam 1230 (as seen by the curved arrow 1420 in FIG. 14). This causes the needle 770 to spin in that same direction (a counter-clockwise direction as shown in FIG. 14, but the present invention is also applicable to a rotation of the needle 770 in a clockwise direction).

Figure 15:
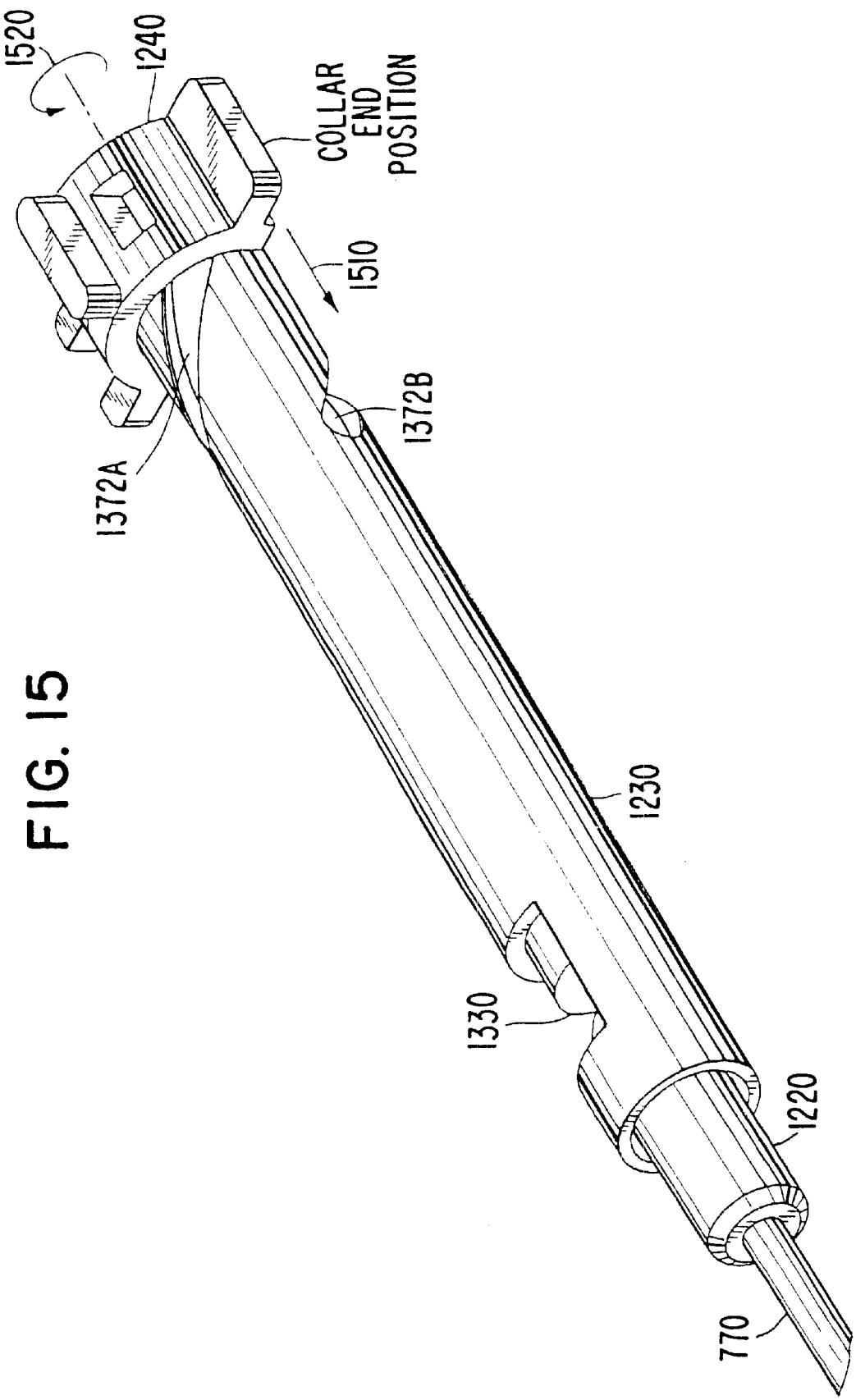
FIG. 15 shows a view similar to that shown in FIG. 14, but whereby the needle assembly and needle cam have each been rotated 180 degrees by movement of the collar attached to the needle cam, according to an embodiment of the present invention.

FIG. 15 shows the position of the needle hub 1220 and needle cam 1230 after the collar 1240 has been moved from its most distal position to its most proximal position with respect to the main body of the medical instrument 700. The collar 1240 will return to its home, or most distal position, for the next trigger cycle (that is, next seed implant cycle). To return to its home position, the needle 770 will rotate or spin in a clockwise direction, to return back to the position as shown in FIG. 14.

In the preferred embodiment, the movement of the control link 2020 is caused by a gear assembly and other linkage components within the main body of the medical instrument 700, whereby the needle 770 is caused to spin by movement of the control link 2020 in a direction as shown in FIG. 20. The needle spin occurs after a seed has been implanted, at a time when the medical instrument 700 is being retracted to a next seed implantation position for implanting seeds within the patient's body. In the present invention, the needle spin will also occur after the medical instrument 700 has indexed to the next seed implantation position, whereby the needle 770 will spin in place back to its initial angular position with respect to the medical instrument 700.

As explained above, the control link 2020 is coupled, by way of various coupling elements (not shown), back to a drive rack assembly (not shown) located within the medical instrument 700, whereby the stroke of the control link 2020 is controlled by movement of the drive rack assembly (which in turn is caused by movement of the trigger 180 on the handle 705 of the medical instrument 700). Details of the various coupling elements are not discussed herein, in order to provide a more clearer description of the present invention as it relates to a needle hub configuration and to a needle spin configuration.

In the present invention, regardless of the amount of index pitch, that is, regardless of the amount that the medical instrument 700 moves between consecutive seed implantation positions, the needle 770 spins the same amount (180 degrees in the preferred embodiment, but other amounts of spin may be envisioned) during that movement of the medical instrument.

In an embodiment of the present invention, there are five possible pitch settings for the medical instrument 700, whereby a particular pitch setting is effected by actuation of the pitch adjustment knob 170 at the proximal end of the medical instrument 700. In the preferred embodiment, the minimum pitch index is 5 mm, and the maximum pitch index is 15 mm. Other numbers of pitch settings are possible (e.g., two to twenty), and other minimum and maximum pitch sizes are possible, while remaining within the scope of the invention as described herein. Regardless of which pitch setting is being used, the needle 770 rotates 180 degrees during the movement of the medical instrument 700 to a next seed implantation position.

Figure 16A:
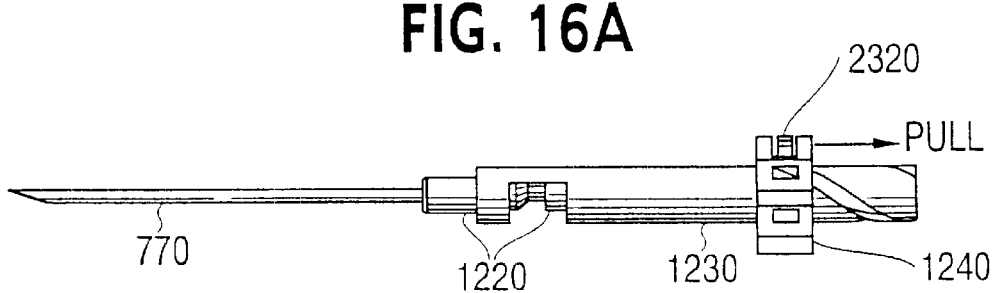
FIGS. 16A and 16B show top and side views, respectively, of the needle spin assembly and needle coupling assembly, when the needle assembly is in a start (unrotated) position, according to an embodiment of the present invention.
Figure 16B:
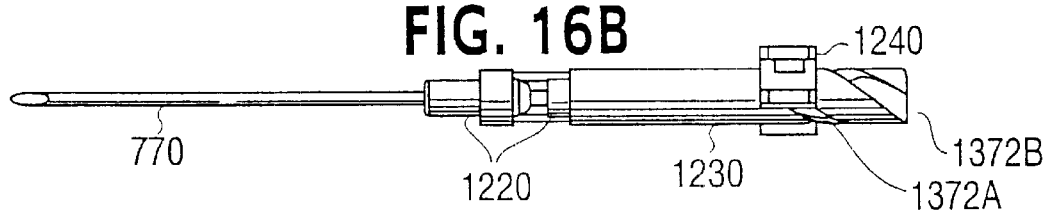
Figure 16C:
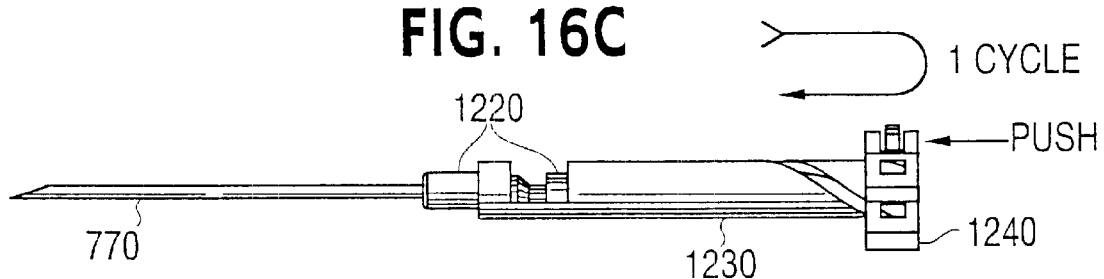
FIGS. 16C and 16D show top and side views, respectively, of the needle spin assembly and needle coupling assembly, when the needle assembly is in an end (fully rotated) position after one needle spin cycle, according to an embodiment of the present invention.
Figure 16D:
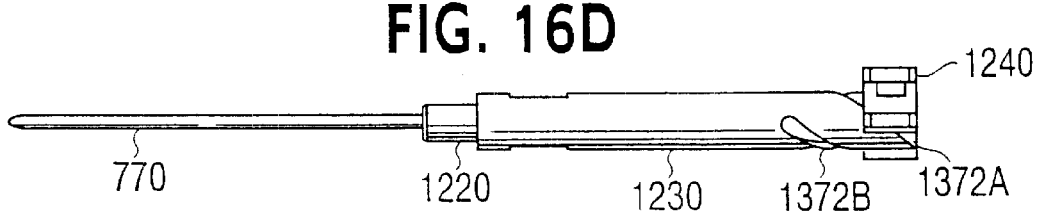

FIGS. 16A and 16B respectively show a top view and a side view of the needle hub assembly 1200 in the start position (collar 1240 at its most distal position on the needle cam). FIGS. 16C and 16D respectively show a top view and a side view of the needle hub assembly 1200 in an end position, which occurs after one seed implantation cycle. The collar 1240 has been pulled to its most proximal position on the needle cam 1230, whereby it will release back to its most distal position, to complete the cycle, and to set up for a next seed implantation cycle.

The two helical slots 1372A, 1372B of the needle cam 1230 can be seen in FIGS. 16B and 16D; and opposing pins of the collar 240 ride along these slots by operation of the control link 2020.

FIGS. 17A and 17B are similar to FIGS. 16A and 16B, whereby two cross sectional cuts are shown in FIG. 17B. Those cross sectional views are shown in FIGS. 17E and 17F. FIG. 17C shows a front view of the collar 1240 attached to the needle cam 1230, whereby a cross sectional cut in also shown in that figure. That cross sectional view is shown in FIG. 17D. FIG. 17G shows a bottom view of the collar 1240 and needle cam 1230 being coupled to each other.

FIG. 17F shows the registration of the cam registration ribs 1355 of the needle cam 1230, with the needle registration ribs 1340 of the needle hub 1220.

FIG. 17E shows the two opposing pins of the collar 1240 that are engaging the respective slots 1372A, 1372B of the needle cam 1230. The two opposing pins 1372A, 1372B of the collar 1240 are positioned 180 degrees apart. A conduit 1710 running along the longitudinal center axis of the needle cam 1230 is the region through which the seed and pusher wire (or stylet) pass through, in order to place a seed at a distal end of the needle cannula 770.

In more detail, referring now to the cross-sectional view of FIG. 24, a stylet (also called a "pusher" hereinbelow)

2410 pushes a seed 2420 from a shuttle 2430 (shown in its extended position in FIG. 24) to the distal end 772 of the needle 770. When the medical instrument 700 is retracted to a next seed implantation position, the seed 2420 exits the needle cannula 770 and is left within a particular location within the patient's body (e.g., within some tissue), to thereby provide treatment for the patient.

The diameter of the conduit 1710 is preferably slightly larger (e.g., a few thousandths of an inch) than the diameter of the seed 2420 (typically a cylindrically-shaped object), so that the seed 2420 will be slid along the path of the conduit 1710 through the needle cam 1230, and thereby pass through most of the needle cannula 770 to be deposited at its distal end 772. FIG. 17D shows the longitudinal view of the path that the seed 2420 takes from the distal end of the main body of the medical instrument 700, through the needle cam 1230 and thereby into the needle cannula 770 that is coupled to the needle cam 1230 by way of the needle hub 1220.

Figure 24:
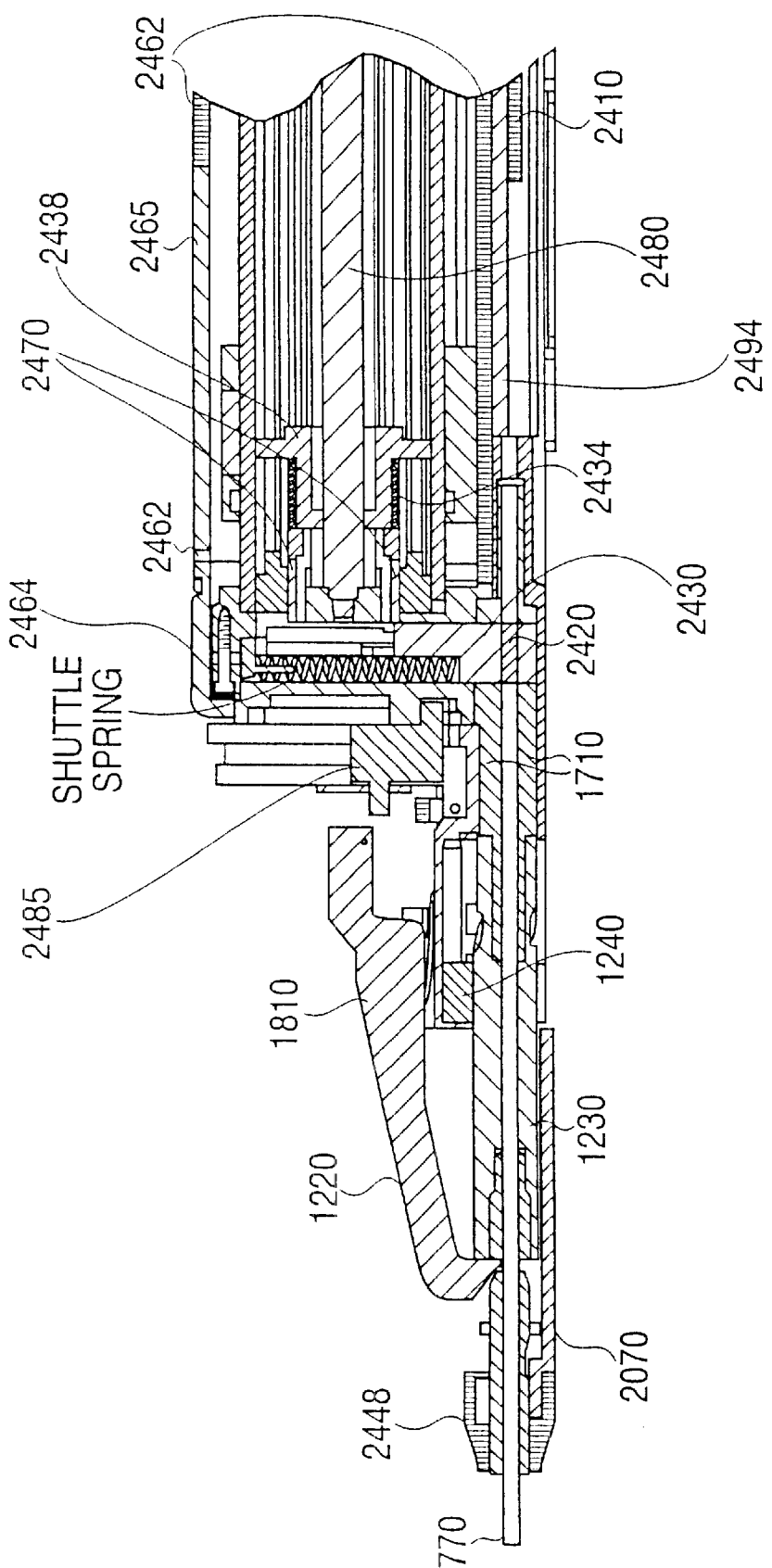
FIG. 24 shows a cross-sectional view of the distal portion of the medical instrument, with a cartridge disposed within the medical instrument and with a needle assembly being coupled to the medical instrument, according to an embodiment of the invention.

FIG. 24 shows the path that the seed 2420 takes from the extended shuttle 2430, through a conduit-frame 1710, through the needle cam 1230, through the needle hub 1220, and then through the needle cannula 770 to be disposed at its distal end 772. The conduit-frame 1710 is preferably press fitted onto a plastic feature (not shown, but may be a plastic protrusion) at the distal end of the medical instrument 700.

FIG. 24 shows the distal frame 2070 of the medical instrument 700, which holds the needle cam 1230 and needle hub 1220 in place at the distal end of the medical instrument 700. There is also shown a nozzle cap 2448 that affixes to a distal end of the distal frame portion 2070. The distal end of the medical instrument 2070 is shared with the other body parts, and the nozzle cap 2448 helps hold those parts in place.

When inserted in the medical instrument 700, the cartridge 110 is disposed at the distal region within the medical instrument 700, as shown in FIG. 24. The cartridge 110 includes a lens portion 2465 at a top surface thereof, for displaying the current number of seeds remaining in the cartridge 110. A seed 2470 at a top conduit of the cartridge 110, and a seed 2470 at a bottom conduit of the cartridge 110, are also shown in FIG. 24. The seeds 2470 are urged to the distal end of the cartridge 110, by a pusher spring 2434 and a cartridge pusher 2438. Details of the operations of these elements is provided in the CARTRIDGE-MOVEABLE SHIELD application, mentioned previously.

A center rod 2480 is also shown in FIG. 24, which passes through the center axis of the cartridge 110 and which is part of a mechanism by which the cartridge 110 rotates to thereby provide a seed from a different conduit to a seed extraction position (to thereby be provided to a seed accepting hole in a shuttle that is in a retracted position within the cartridge). Details of how the cartridge 110 rotates are provided in the related CARTRIDGE-MOVEABLE SHIELD application, mentioned previously.

FIG. 24 also shows a reset shuttle link 2485 at the distal end of the medical instrument 700, which is provided so as to allow the operator to reset the shuttle 2430 back to its closed position within the main body of the cartridge 110. In FIG. 24, the cartridge 110 is shown having a proximally-located cup 2462 and a distally-located cap 2464, whereby the cup and cap are affixed to each other to provide an outer housing for the cartridge 110. This configuration of the cartridge 110 is slightly different from the configuration shown in FIG. 11, which has a top housing 5 and a bottom housing 4. In the cartridge configuration shown in FIG. 24, the cartridge outer housing is divided into proximal and distal portions, as opposed to top and bottom portions. As shown in FIG. 24, the lens 2465 of the cartridge 110 is provided on a top surface of the cup, when the cartridge 110 is properly positioned within the medical instrument 700. The lens provides for an operator to clearly discern the number of seeds remaining in the seed cartridge 110, by way of a seed count number that is visible to the operator through the lens 2465. See the CARTRIDGE-MOVEABLE SHIELD application for more details on this feature of the cartridge 110.

Figure 22A:
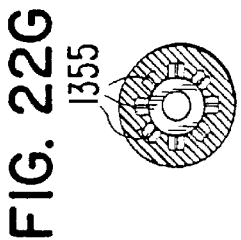
FIGS. 22A, 22B, 22C and 22D show side, top, front and back views, respectively, of the needle assembly according to an embodiment of the present invention.
Figure 22B:
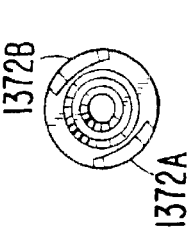
Figure 22C:
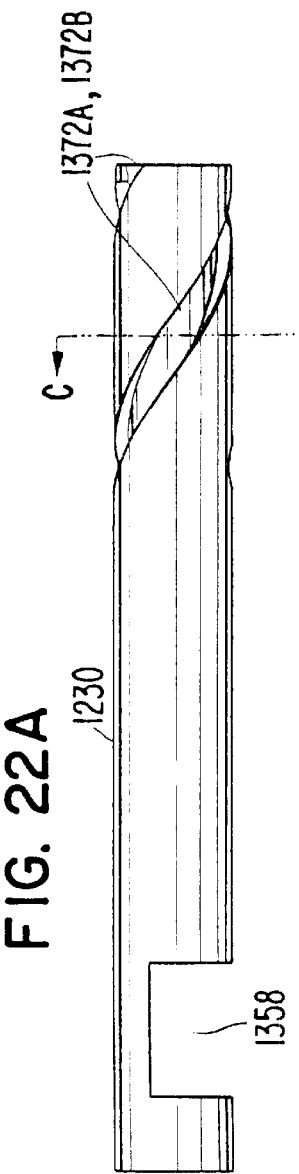
Figure 22D:
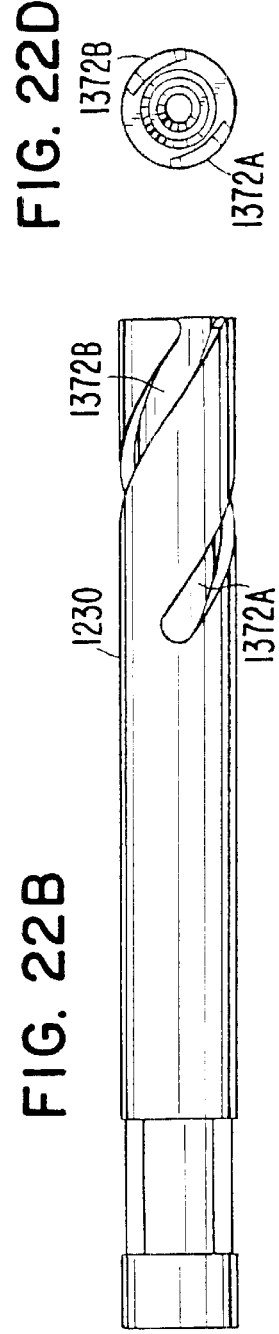
Figure 22E:
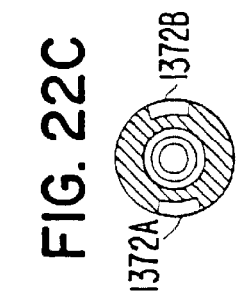
FIGS. 22E, 22F and 22G show separate cross sections obtained from FIGS. 22A, 22C and 22D, according to an embodiment of the present invention.

Referring now to FIG. 22A, the conduit-frame 1710 is preferably a metal part or protrusion located at the distal end of the main body of the medical instrument 700. The metal composition of the conduit-frame 1710 protects the user from any radiation emanating from the seed as it passes through from the extended shuttle 2430 to the needle cannula 770, with the stylet 2410 pushing the seed along that path. The needle cam 1230 is fitted onto the conduit-frame 1710, to thereby couple the needle cam 1230 to the main body of the medical instrument 700 (due to the conduit-frame 1710 being press fitted or insert molded to the frame of the medical instrument 700), with the needle cam 1230 resting on the distal frame portion 2070 of the medical instrument 700 (see FIG. 19, for example). Also shown in FIG. 24 is a pusher guide 2494, which is an element of the medical instrument frame that maintains the stylet 2410 in its proper position when it is extended. The stylet 2410 is shown in its non-extended position in FIG. 24.

A seed implantation process will now be described. By operation of a seed extraction button on the medical instrument 700, a seed is placed into the shuttle 2430 of the seed cartridge 110 provided within the medical instrument 700, and then the shuttle 2430 is extended out from the main body of the seed cartridge 110, via actuation of the seed transfer button 185. By operation of the trigger 180 on the handle 705 on the medical instrument 700 from a first (start) position to a second (intermediate) position, the stylet 2410 is made to extend through a hole in the shuttle 2430 in which the seed is positioned. The stylet 2410 pushes the seed 2420 through the conduit-frame 1710, through the conduit 1710 in the needle cam 1230, and then into the needle cannula 770, to thereby be placed at its proper position at the distal end 772 of the needle cannula 770. Alternatively, if a trocar needle is used, the stylet 2460 would position the seed 2420 at a distal end of the trocar needle.

With the seed 2420 at its proper position, the operator actuates the trigger 180 from its second position to a third position (maximally extended position), to move the medical instrument 700 to a next seed implantation position, whereby the needle 770 is spun during this movement of the medical instrument 700. With the stylet 2410 maintained directly behind the seed at the distal end of the needle cannula 770, and with the needle cannula 770 being spun during the movement of the medical instrument 700 to the next seed implantation position, the seed is caused to exit the needle cannula 770 into a proper location within the patient's body, and to stay in place even after the medical instrument 700 moves to a new position.

The inner diameter (ID) of the needle cannula 770 is preferably slightly larger than the size of the seeds that are to be implanted into a patient. The stylet 2410 is cylindrical in shape, and preferably has a diameter that is slightly larger than the seed diameter (which is also preferably cylindrical in shape). Of course, the stylet 2410 can be sized so that it's diameter is the same or substantially the same size as the seed's diameter, or even slightly smaller. Alternatively, the stylet 2410 may be a hollow cannula instead of a solid wire, to assist in venting trapped air.

Figure 23A:
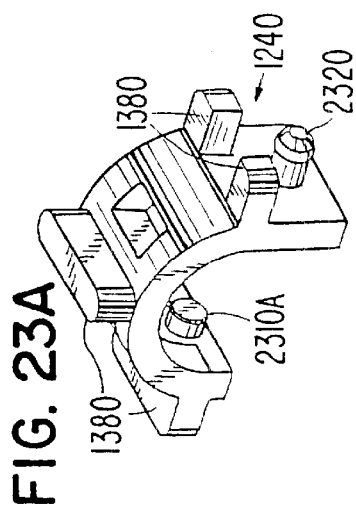
Figure 23B:
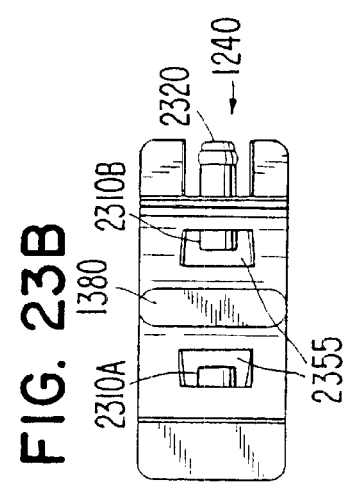
Figure 23D:
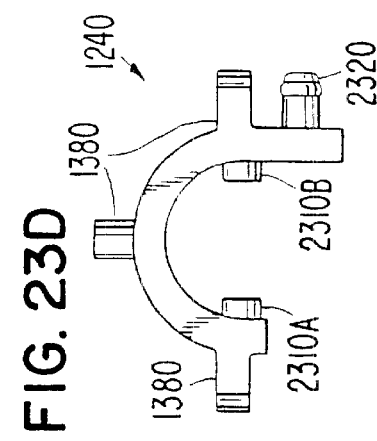
Figure 23E:
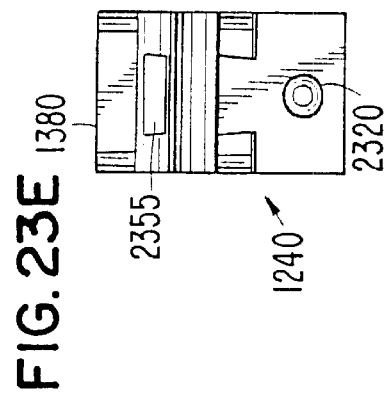
Figure 23C:
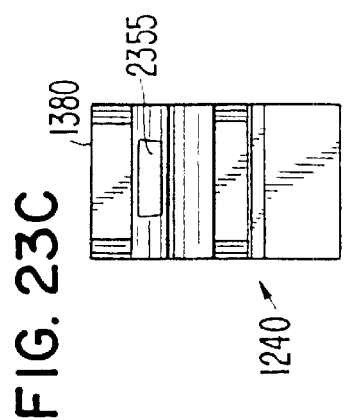
Figure 23F:
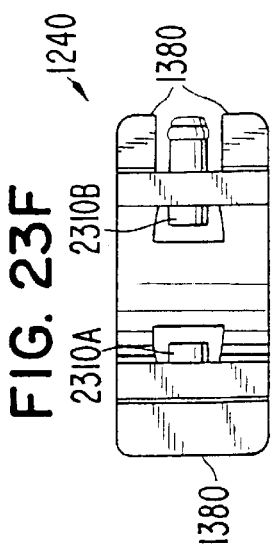

FIG. 23A shows a perspective view of the collar 1230. FIG. 123B shows a top view, FIG. 23C shows a left side view, FIG. 23D shows a front view, FIG. 23E shows a right side view, and FIG. 23F shows a bottom view of the collar 1230. The collar 1230 includes anti-rotation ribs 1380 on the left side, the right side, and a top side of the collar 1240. The anti-rotation ribs 1380 maintain the collar 1240 in place within the distal frame portion 2070 of the medical instrument 700. FIG. 20 shows the collar 1240 in position within the distal frame portion 2070. A slot within the distal frame portion 2070, not shown due to the needle cam 1230 blocking it in FIG. 20, is provided to allow the top slot of the collar 1240 to ride therein.

Referring back to FIGS. 23A to 23F, the collar 1240 is shown having two openings 2355, or windows, at a top portion thereof. The openings 2355 are provided only to allow an easier molding of the collar 1240 during a manufacturing process for creating the collar 1240, and the openings 2355 do not serve any other purpose. Also, the two separate anti-rotation ribs 1380 on one side of the collar 1240 are also there solely for allowing an easier molding of the collar 1240 (to allow the control link attachment pin to be formed on the collar 1240 during a manufacturing process). As such, other types of anti-rotation ribs, as well as other configurations of the collar 1240, may be envisioned, while remaining within the scope of the invention as described herein.

As discussed above, the control link attachment pin causes the collar 1240 to move by it being fitted within a hole of the control link 2020. As such, linear movement of the control link 2020 results in linear movement of the collar 1240, which results in a turning, or rotational, movement of the needle cam 1230 and thereby results in a turning or rotational movement of the needle assembly 1225 coupled to the needle cam 1230.

Figure 19:
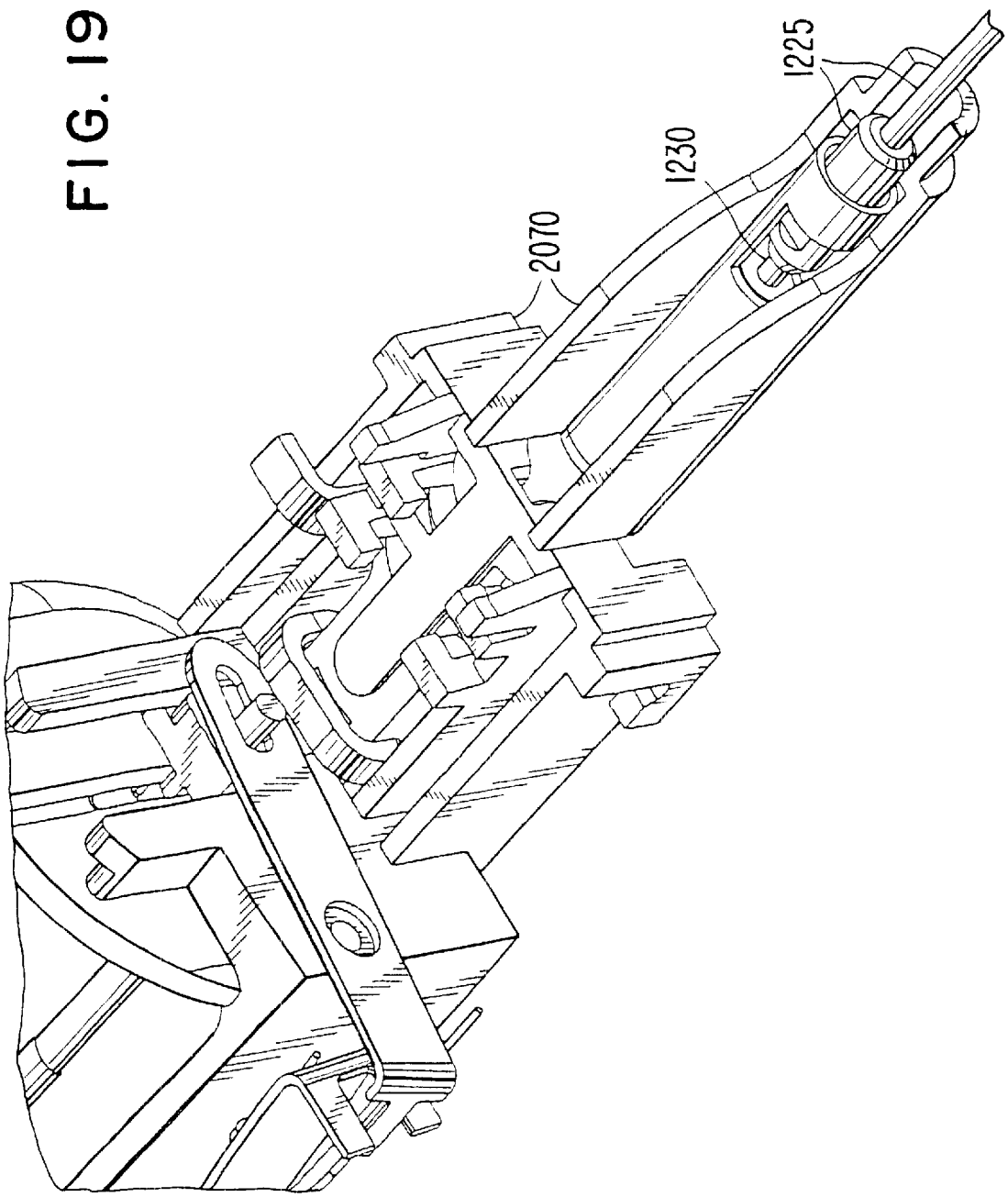
FIG. 19 shows the same view as FIG. 18, but with the needle release arm removed to show a more unobstructed view of the coupling of the needle assembly to the needle cam housed in a distal frame portion of a medical instrument, according to an embodiment of the present invention.

FIG. 19 shows the needle hub assembly in place within the distal frame portion 2070 of the medical instrument 700, and FIG. 18 shows the same needle hub assembly in place, with the needle release arm 1810 also being shown in a "down" position to thereby help hold the needle assembly 1225 in place in the distal frame portion 2070. The distal end of the needle release arm 1810 fits within the needle retention slot 1330 of the needle assembly 1225, when the needle release arm is in the down position. Upon actuation of the release link actuation cam 1814, the needle release arm 1810 pivots about a pivot point 1855 (see FIG. 18), and raises up a slight amount out of the needle retention slot 1330. That way, the needle hub 1220 and needle cannula 770 can be removed from the needle cam 1230, and thereby separated from the medical instrument 700.

The position of the needle cannula 770 (e.g., its depth and location within a patient's body) is typically carefully made in a pre-plan, so that it is undesirable to move the needle position during the coupling of the medical instrument 700 to the needle cannula 770. Typically, the needle cannula 770 is held in place by one hand of the operator, while the medical instrument 700 is held in place by the other hand, whereby the medical instrument 700 is coupled to the needle cannula 770 by way of the needle hub configuration described above.

If any misalignment exists during the coupling of the needle cannula 770 onto the medical instrument 700, that can be overcome (to thereby provide a proper coupling of the needle to the medical instrument) by any of the following configurations: 1) the needle hub 1220 can be configured to readily rotate (while the needle cam 1230 remains fixed in position) to allow slight rotation of the needle cannula 770 within the tissue of the patient to allow proper alignment and coupling of the needle cannula 770 to the medical instrument 700, 2) manual rotation of the needle hub 1220 (and thereby the needle cannula 770) can be performed in order to get a proper alignment of the ribs of the needle hub 1220 with the ribs of the needle cam 1230, 3) a sloppy fit between the ribs of the needle hub 1220 and the ribs of the needle cam 1230 may be provided to allow for coupling of these two elements to each other; or 4) a sloppy fit of the collar pins of the collar 1240 and the helical slots 1372A, 1372B of the needle cam 1230 may be provided to allow a proper coupling of the needle cannula 770 with the medical instrument 700.

In the first configuration described above, the lead-in chamfers 1320 of the needle registration ribs 1340 allow for coupling of the needle hub 1220 to the needle cam 1230, even if they are slightly misaligned with respect to each other. The lead-in chamfers 1320 cause the needle cannula 770 to rotate slightly within the patient's tissue, when the ribs of the needle hub 1220 are registered to the ribs of the needle cam 1230. In this configuration, the needle cam 1230 does not rotate during the alignment procedure.

In the second configuration described above, the needle cannula 770 is manually rotated to place it in proper alignment for coupling the needle hub 1220 to the needle cam 1230. For example, an operator holds the needle cannula 770 in one hand, and holds the medical instrument 700 in his/her other hand. Then, the operator rotates the needle cannula 770 to align the ribs of the needle hub 1220 (attached to the needle cannula 770) to the ribs of the needle cam 1230. In this configuration, the ribs of the needle cam 1230 and the ribs of the needle hub 1220 provide a relatively snug fit, when the needle hub 1220 is coupled to the needle cam 1230.

In the third configuration described above, the registration ribs of the needle cam 1230 and the needle hub 1220 are sized and positioned to allow a somewhat loose fit, so that the needle cam 1230 will rotate or the needle cannula 770 will rotate slightly, to obtain a proper alignment position. For example, if three ribs are provided on the needle cam 1230 and the needle hub 1220, and whereby there is much room between adjacent ribs, the needle hub 1220 can be loosely fit within the needle cam 1230, with space between the engaged ribs. This results in some lost motion during needle spin, e.g., 45 degrees lost motion. However, this lost motion is not a problem due to the large amount of needle spin provided, and whereby the needle coupling procedure is made easier as a result of the loose fitting ribs.

In the fourth configuration described above, the fit between the pins of the collar 1240 and the helical slots on the needle cam 1230 that they ride within, can be made such that the helical slots are slightly larger (e.g., 15 to 20 thousandths of an inch) in width than the size of the pins, to allow for a small amount of rotation (e.g., a few degrees of rotation) of the needle cam 1230. Thus, any slight misalignment of the needle cannula 770 with respect to the needle hub 1220 during a needle/medical instrument coupling procedure can be accommodated.

Any one or more of the above-described four configurations may be utilized with the present invention, to assure a proper alignment of the needle 770 onto the medical instrument 700.

Turning back to FIG. 18, when the release link actuation cam 1814 is actuated to allow the needle assembly 1225 to be removed from the needle cam 1230, the needle release arm 1810 raises up slightly above the needle cam 1230. For example, by way of example and not by way of limitation, the needle release arm 1810 raises 0.010" to 0.050" above the outer surface of the needle cam 1230. This allows the needle hub 1220 and the needle cannula 770 to be removed from the needle cam 1230, such as by pulling the needle cannula 770 in a direction away from the medical instrument 700.

FIG. 20 shows a bottom view of the needle applicator assembly, whereby the positioning of the collar 1240 within the distal frame 2070 of the medical instrument 700, as well as the coupling of the control link 2020 to the collar 1240, can readily be seen.

As seen in FIG. 1, the medical instrument 700 includes a handle 705, which has a trigger 180 which is actuated by an operator, in order to position seeds from the cartridge 110 (placed within the medical instrument 700) to a distal end of a needle coupled to the medical instrument 700. The trigger 180 is in an unengaged position in FIG. 1, which corresponds to a Position A ("home" position). The trigger 180 is moved to a middle Position B, and eventually to a Position C, which is the furthest allowable actuation of the trigger 180. Upon release of the trigger 180, it returns back to its "home" Position A, passing Position B along the way. Position B is preferably positioned approximately halfway between Position A and Position C. Movement of the collar 1240 on the needle cam 1230 happens between trigger Position B and Position C, and then on the return stroke from Position C to Position B.

Due to the actuation of the trigger 180 from Position A to Position B, the stylet 2410 within the medical instrument 700 pushes the seed 2020 from the shuttle 2430 that is in an extended position with respect to the cartridge 110 disposed within the medical instrument 700. The stylet 2410 pushes the seed 2420 through the conduit of the needle cam 1230, and all the way to the distal end 772 of the needle cannula 770. The medical instrument 700 does not move at all during this time.

Now, due to the actuation of the trigger 180 from Position B to Position C, the stylet stays in its most-forward position, and the medical instrument 700 indexes back to a next seed implantation position, while at the same time the needle 770 spins due to the movement of the collar from its most-distal position (relative to the main body of the medical instrument 700) to its most proximal position. This causes the seed located at the distal end of the needle to be released to a proper location within a patient's body (e.g., within a specific location of a prostate gland).

Next, upon release of the trigger 180 by the operator, the trigger 180 returns from Position C to Position B. This results in the collar 1240 moving from its most proximal position to its most distal position, thereby resulting in needle spin (in the opposite direction than what occurred during Position B to Position C movement of the trigger 180). The medical instrument 700 does not move at this time.

Finally, when the trigger 180 travels from Position B to its home Position A, the stylet 2410 returns back to its most proximal position within the main housing of the medical instrument 700, and the shuttle retracts back within the cartridge 110 (after the stylet passes back through it and thereby clears the shuttle). This sets up the medical instrument for a next seed implantation operation, at a next seed implant location within the patient's body.

As explained earlier, due to the surrounding tissue at a seed implantation position, and due to the spinning of the needle to a next seed implantation position, the surrounding tissue will effectively grab the seed so that the seed leaves the needle cannula, while at the same time the seed is not sucked in the direction of movement of the needle cannula due to the spinning motion of the needle cannula.

FIGS. 21A through 21E show different views of the needle hub assembly. FIG. 21A is a top view, FIG. 21B is a side view, FIG. 21C is a front view, FIG. 21D is a back view, and FIG. 21E is a perspective view. FIG. 21E shows the needle hub 1220 without the needle cannula 770 coupled to it. A lead-in chamfer 2178 is provided at the proximal end of the needle hub 1220, so that the stylet 2410 will not get caught against the inner surface of the needle hub 1220, but rather will ride up on the lead-in chamfers 2178 to a proper position, when its makes it way to the distal end 772 of the needle cannula 770.

Figure 22F:
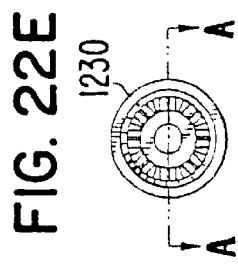
Figure 22G:
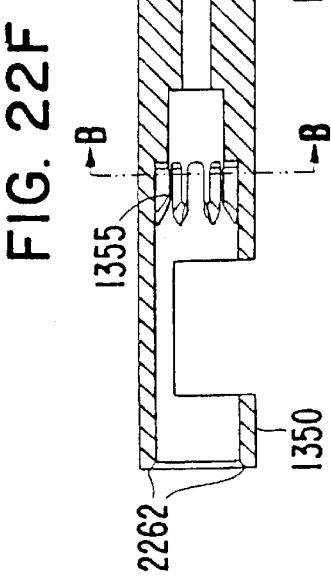

FIGS. 22A through 22G show various views of the needle cam 1230, in which the helical cam slots can be readily seen in FIGS. 22A, 22B, 22C and 22D. Also, the registration ribs 1355 within the inner surface of the needle cam 1230 can be readily seen in FIGS. 22F and 22G. FIG. 22F also shows a chamfer lead-in 2262 to the conduit-frame 1710, to ensure that the stylet 2410 and the seed 2420 being pushed by the stylet 2410 do not get caught up on the distal end of the needle stabilizer collar 1350 (see also FIG. 13) when the seed 2420 is pushed all the way to the distal end 772 of the needle cannula 770.

While the above components are described with respect to the preferred embodiment, other similar types of components may be utilized, while remaining within the spirit and scope of the present invention, as exemplified by the claims. For example, other types of medical procedures using implantation devices, whether they be seeds or other things, and whether they are for treating prostate cancer or something else, may be utilized based on the teachings provided above. For example, while the embodiments described above show two helical slots on the needle cam, one of ordinary skill in the art would recognize that the coupling of the collar to the needle cam may be performed by way of one helical slot or more than two helical slots, for example.

What is claimed is:

1. An apparatus for coupling a needle to a medical instrument, comprising:

a needle hub that is coupled to the needle, the needle hub having a plurality of cam registration ribs on an outer surface thereof; and a needle cam that has a plurality of hub registration ribs on an inner surface thereof; and a needle nozzle disposed at a distal end of the medical instrument, the needle nozzle being configured to hold the needle cam in place within the needle nozzle, wherein the cam registration ribs are fitted between the hub registration ribs to provide a coupling of the needle to the medical instrument.

2. An apparatus for coupling a needle to a medical instrument, comprising:

needle hub means for attaching to a proximal end of the needle;

needle cam means for accepting the needle hub means for coupling thereto, wherein said needle cam means is disposed in a frame of the medical instrument at a distal end thereof.

3. The apparatus according to claim 2, wherein said needle cam means includes an opening, said apparatus further comprising:

needle arm registration means for holding the needle hub means in place when said needle hub means is coupled to said needle cam means, said needle arm registration means being positioned within the opening when in a closed position.

4. A method for coupling a needle to a medical instrument, comprising:

attaching a needle hub to the needle, the needle hub including first registration ribs on an external surface thereof;

registering the first registration ribs of the needle hub with second registration ribs on an inner surface of a needle cam disposed on a distal frame portion of the medical instrument, wherein the needle hub is coupled to the needle cam as a result, thereby coupling the needle to the medical instrument in a non-integral manner.

5. The method according to claim 4, further comprising:

placing a needle attachment arm to an opening within the needle hub, to thereby help maintain the needle hub to be coupled to the needle cam.

* * * * *